US012740720B2

(12) United States Patent
Ranta et al.

(10) Patent No.: US 12,740,720 B2
(45) Date of Patent: Sep. 22, 2026

(54) SYSTEM, METHOD AND COMPUTER PROGRAM FOR MONITORING HEALTH OF A PERSON

(71) Applicant: MERU HEALTH OY, Helsinki (FI)

(72) Inventors: Kristian Ranta, Helsinki (FI); Albert Nazander, Helsinki (FI)

(73) Assignee: MERU HEALTH OY, Helsinki (FI)

( * ) Notice: Subject to any disclaimer, the term of this patent is extended or adjusted under 35 U.S.C. 154(b) by 347 days.

(21) Appl. No.: 18/554,499

(22) PCT Filed: Apr. 11, 2022

(86) PCT No.: PCT/FI2022/050235
§ 371 (c)(1),
(2) Date: Oct. 9, 2023

(87) PCT Pub. No.: WO2022/219236
PCT Pub. Date: Oct. 20, 2022

(65) Prior Publication Data

US 2024/0188846 A1 Jun. 13, 2024

(30) Foreign Application Priority Data

Apr. 12, 2021 (FI) ...................................... 20215427

(51) Int. Cl.
*A61B 5/00* (2006.01)
*A61B 5/024* (2006.01)
*A61B 5/08* (2006.01)

(52) U.S. Cl.
CPC ........ *A61B 5/0816* (2013.01); *A61B 5/02405* (2013.01); *A61B 5/486* (2013.01); *A61B 5/7264* (2013.01)

(58) Field of Classification Search
CPC ... A61B 5/0816; A61B 5/02405; A61B 5/486; A61B 5/7264; A61B 5/02416; A61B 5/024; A61B 5/08; A61B 5/0205
See application file for complete search history.

(56) References Cited

U.S. PATENT DOCUMENTS 6,212,427 B1 4/2001 Hoover
2006/0004265 A1* 1/2006 Pulkkinen ............ A61B 5/0205 600/300

(Continued)

FOREIGN PATENT DOCUMENTS

WO 2016061513 A1 4/2016
WO 2019240778 A1 12/2019
WO 2020181297 A2 9/2020

OTHER PUBLICATIONS

International Search Report issued by the Finnish Patent and Registration Office acting as the International Searching Authority in relation to International Application No. PCT/FI2022/050235 dated Jun. 14, 2022 (5 pages).

(Continued)

*Primary Examiner* — May A Abouelela
(74) *Attorney, Agent, or Firm* — Carter, DeLuca & Farrell, LLP

(57) ABSTRACT

A system for monitoring health of a person during a health monitoring session (s) is disclosed. System includes a breathing pacer configured to indicate breathing information to the person, the breathing pacer arranged to operate in a controlled mode, the controlled mode including timing breathing events to the person, and in a variable mode, the variable mode including indicating information related to a resonance score RS to the person. Breathing information is determined by fitting a periodic biofeedback function into the instantaneous heart rate data within time window (w) to determine the parameters of the periodic biofeedback func- (Continued)

tion at the timepoint (t) and the cumulative difference E at the timepoint (t). A related method and computer program are also disclosed.

18 Claims, 11 Drawing Sheets

(56) References Cited

U.S. PATENT DOCUMENTS

| | | | | |
|---|---|---|---|---|
| 2013/0338460 | A1* | 12/2013 | He | A61B 5/0006 600/479 |
| 2015/0182129 | A1 | 7/2015 | Colley et al. | |
| 2016/0374567 | A1* | 12/2016 | Breslow | A61B 5/02405 600/301 |
| 2017/0049392 | A1* | 2/2017 | Brattain | A61B 7/003 |
| 2018/0220957 | A1 | 8/2018 | Fuerst et al. | |
| 2018/0289285 | A1* | 10/2018 | Vardas | A61B 5/0816 |
| 2021/0307679 | A1* | 10/2021 | Saalasti | G06N 3/0499 |

OTHER PUBLICATIONS

Written Opinion of the International Searching Authority issued by the Finnish Patent and Registration Office acting as the International Searching Authority in relation to International Application No. PCT/FI2022/050235 dated Jun. 14, 2022 (9 pages).

Finnish Search Report issued by the Finnish Patent and Registration Office in relation to Finnish Application No. 20215427 dated Aug. 10, 2021 (1 page).

* cited by examiner

SYSTEM, METHOD AND COMPUTER PROGRAM FOR MONITORING HEALTH OF A PERSON

CROSS-REFERENCE TO RELATED APPLICATIONS

This application is a national phase entry under 35 U.S.C. 371 of PCT International Application No. PCT/FI2022/050235 filed Apr. 11, 2022, which claims priority to Finnish Patent Application No. 20215427, filed Apr. 12, 2021, the disclosure of each of these applications is expressly incorporated herein by reference in their entirety.

FIELD OF THE INVENTION

The present invention relates to a system for monitoring health of a person. The present invention relates also to a method for monitoring health of a person. The present invention relates also to a computer program for monitoring health of a person.

BACKGROUND OF THE INVENTION

Vagus nerve is an important nerve in the human body and it plays a major role in the correct functioning of the parasympathetic nervous system. In the medical community, stimulation of the vagus nerve is believed to lead to various cardiovascular, cerebrovascular, metabolic and other physiological and mental health benefits.

In the prior art, vagus nerve has been stimulated in a non-invasive way for example by application of electricity to the frontal neck area of the human body. Devices to this purpose are commercially available, and they resemble an electrical razor apparatus in size and shape. Also invasive ways of vagus nerve stimulation exist. As an example, a device may be surgically implanted under the skin of a person's chest, and a wire may be threaded under the skin to connect the device to the vagus nerve. When activated, the device sends electrical signals along the vagus nerve to person's brainstem, activating the vagus nerve and the nervous system in general.

It is also known that breathing in a certain, in general, slow breathing rate may stimulate the vagus nerve favourably. As one way to stimulate the vagus nerve favourably, breathing, during a so-called breathing exercise, with a certain slow breathing rate offers many advantages. Breathing correctly by a person involves no invasive or non-invasive electrical stimulation of the nerve which can be difficult to arrange especially if the related arrangements require surgical procedures or dedicated electrical devises, or both. However, monitoring the breathing with the prior art devices and systems is challenging as monitoring breathing requires its own set of dedicated devices. These devices may be based, for example, to the analysis of flow of breathing inhalations and exhalations and to the movement of breathing gasses in the respiratory tract, for example mouth or nose. Clearly, wearing or holding such metering devices in mouth or by the nose is relatively unpleasant and complex.

It is believed that an effective positive vagus nerve stimulus through breathing is achieved when breathing rate of a person follows the natural heart rate variation of the person. In the medical community, this kind of stimulation is sometimes called "cross-coherence" between breathing and heart rate variation. In general, when a person inhales, the instantaneous heart rate increases, and when a person exhales, the instantaneous heart rate decreases.

Normally at rest, an average heart rate is between 60 and 100 BPM. (beats per minute). However, this is heavily dependent on the gender, age, fitness level and level of relaxation of the person. Heart rate variations and breathing are also personal traits and there is no one universal value for a correct breathing rate to achieve strong vagus nerve stimulus through cross-coherence. Instead, every person has his or her own best breathing rate that best matches the heart rate variability ("HRV") and breathing. Usually, the breathing rate that may provide the strongest vagus nerve stimulus is between 3 and 8 breaths in one minute. In general, a high variability in the heart rate may be an indication of a strong vagus nerve stimulation with positive health effects.

In the prior art, there are some notions of analysing the cross-coherence of breathing rate and heartbeat rate of a person and of giving information to the person to find the best breathing rate for a person to reach a high heart rate variability that may indicate strong vagus nerve stimulation. This has involved the usage of Fourier transforms and complex signal processing techniques to indicate spectral characteristics of heart rate variation and breathing. To get reliable spectral data, a very long dataset comprising data of instantaneous heart rates and breathing spanning several minutes has been needed. This makes the practical implementation of the system very difficult as the person whose breathing and heartbeats are monitored needs to remain in complete rest, and at the same time, pay attention to the way he/she breathes and, possibly, alter the way he/she breathes for several minutes.

Preferably, vagus nerve stimulation through breathing is attempted frequently, somewhat like a repeated fitness routine or exercise, as the positive health effects may grow gradually stronger. With repeated breathing exercises, a person may achieve the health benefits faster during the exercise. Optimal breathing rate for vagus nerve stimulation may also decrease somewhat over time. Clearly, a comfortable and fast approach for determining the heart rate variation, and a related indication of the strength of the related vagus nerve stimulation through breathing is needed.

Thus, at least two prior art problems can be raised: Stimulating the vagus nerve requires complex devices and procedures and there is a clear need to overcome the above-mentioned problems in the prior art. If vagus nerve is to be stimulated with a correct breathing rate and through breathing in general, determining the breathing rate well suited for a person to increase heart rate variability that may stimulate the vagus nerve favourably with prior art methods and devices has been challenging.

BRIEF DESCRIPTION OF THE INVENTION

An object of the present invention is to provide a system, a method and a computer program for monitoring health of a person during a health monitoring session so that the prior art disadvantages are solved or at least alleviated.

The preferred embodiments of the invention are disclosed in the dependent claims.

The present invention is based on an idea of providing a system for monitoring health of a person during a health monitoring session is disclosed. The system comprises a heart rate sensor arranged to measure heart beats of the person for providing heart rate measurement data, a breathing pacer configured to indicate breathing information to the person, the breathing pacer arranged to operate: in a controlled mode, the controlled mode comprising timing breathing events to the person, and in a variable mode, the variable mode comprising indicating information related to a resonance score RS to the person. The system also comprises a data processing system. The data processing system is arranged to provide a predetermined success threshold ET. The data processing system is configured, during a health monitoring session to receive (A) the heart rate measurement data from the heart rate sensor, and analyse (C) the heart rate measurement data such that in the analysis, the data processing system is configured to: calculate (C1) instantaneous heart rate data comprising heart rate of each measured heartbeat, calculating performed over a time window in the health monitoring session, the time window comprising a timepoint t, the instantaneous heart rate data being calculated based on the heart rate measurement data received from the heart rate sensor, provide (C2) a periodic biofeedback function comprising parameters and a cumulative difference E relative to the instantaneous heart rate data, the parameters of the periodic biofeedback function comprising an amplitude A, and fit (C3) the periodic biofeedback function into the instantaneous heart rate data within the time window to determine the parameters of the periodic biofeedback function at the timepoint, the cumulative difference E at the timepoint, and the resonance score RS at the timepoint from the parameters and from the cumulative difference E. The data processing system is also configured, during a health monitoring session to arrange (D) the breathing pacer into the controlled mode to time the breathing events to the person if the resonance score RS does not meet the predetermined success threshold ET, the resonance score RS determined by receiving and analysing the heart rate measurement data, and arrange (E) the breathing pacer into the variable mode if the resonance score RS meets the predetermined success threshold ET, the resonance score RS determined by receiving and analysing the heart rate measurement data.

Accordingly, in (D) the system is configured to arrange the breathing pacer into the controlled mode based on the analyzing in (C).

Further, in (D) the system is configured to compare the determined resonance score RS at the time point to the predetermined success threshold ET and arranged the breathing into the controlled mode if the resonance score RS does not meet the predetermined success threshold ET based on the comparing.

Accordingly, in (E) the system is configured to arrange the breathing pacer into the variable mode based on the analyzing in (C).

Further, in (E) the system is configured to compare the determined resonance score RS at the time point to the predetermined success threshold ET and arranged the breathing pacer into the variable mode if the resonance score RS meets the predetermined success threshold ET based on the comparing.

In some embodiments and according to the above, the system is configured to actively change between the controlled mode and the variable mode based on the determined resonance score and the predetermined success threshold ET.

Advantage of the system is that a breathing frequency of the person that strongly stimulates the vagus nerve is determined quickly when compared to prior art systems, without complex arrangements in the respiratory tract. With controlled mode, a good breathing frequency range for vagus nerve stimulation is found, and then with the variable mode, the person may experiment if an optimal breathing frequency is found.

In an embodiment, in the fitting the data processing system is configured to: determine the cumulative difference E between the instantaneous heart rate data and the periodic biofeedback function within the time window, the time window comprising the timepoint, and perform the fitting based on a calculated minimum of the cumulative difference E within the time window to determine the parameters of the periodic biofeedback function at the timepoint, the time window comprising the timepoint. Fitting a periodic function (here, the periodic biofeedback function) to a measurement data (here, to instantaneous heart rate data) based on a minimum of a cumulative difference is an effective way to achieve the fitting.

In an embodiment, the data processing system is configured perform the fitting within the time window with a least squares method; or a modified least squares method; or a random search; or an exhaustive search; or any combination thereof. These fitting methods are effective methods for performing the fitting and they may be used in combination to avoid the convergence of the fitting method to a local minimum of the cumulative difference instead of a global minimum.

In an embodiment, in fitting and in determining the parameter indicating the amplitude A of the periodic biofeedback function at the timepoint the data processing system is arranged to determine a minimum instantaneous heart rate and a maximum instantaneous heart rate of instantaneous heart rate data within the time window, subtract the minimum instantaneous heart rate from the maximum instantaneous heart rate, divide the value of subtraction by 2, and determine the parameter indicating the amplitude A of the periodic biofeedback function at the timepoint based on the value of the division. For a periodic, alternating function such as the periodic biofeedback function this is an effective way to determine an amplitude parameter of the function, or an initial guess for the amplitude parameter of the function for the fitting method.

The amplitude parameter A is arranged to represent the amplitude A of the periodic biofeedback function at the timepoint and arranged determine the heart rate variability of the person at the timepoint.

The amplitude A of the instantaneous heart rate is arranged to determine the heart rate variability in frequency domain (1/time unit).

In an embodiment, the parameters of the periodic biofeedback function comprise an angular frequency P and in fitting in determining the parameter indicating the angular frequency P of the periodic biofeedback function at the timepoint the data processing system is arranged to determine a cycle time TD of the instantaneous heart rate data within the time window, and determine the parameter indicating the angular frequency P of the periodic biofeedback function at the timepoint based on the cycle time TD. For a periodic, alternating function this is an effective way to determine an angular frequency parameter of the function, or an initial guess for the angular frequency parameter of the function.

In the present invention, the amplitude A of the instantaneous heart rate is configured to indicate or determine the heart rate variability of the person in frequency domain (1/time unit) and is thus a frequency domain characterisation. Further, also the angular frequency P is also configured to indicate or determine angular frequency P of the periodic biofeedback function at the timepoint in frequency domain.

The angular frequency P is arranged to determine the angular frequency P of the periodic biofeedback function at the timepoint in frequency domain.

Utilizing the frequency domain in the biofeedback function enables the simple and fast calculation of the parameters and further quick fitting of the periodic biofeedback function into the instantaneous heart rate data. This further enables nearly real-time feedback to the person.

In an embodiment, the parameters of the periodic biofeedback function comprise a mean M (or mean value M) of the periodic biofeedback function, and in fitting, in determining the mean M of the periodic biofeedback function at the timepoint, the data processing system is arranged to determine a mean value of the instantaneous heart rate data within the time window, and determine the mean M of the periodic biofeedback function at the timepoint based on the mean value. For a periodic, alternating function such as the periodic biofeedback function this is an effective way to determine the parameter indicating the mean of the function, or an initial guess for the parameter indicating the mean of the function.

In an embodiment, the periodic biofeedback function f(t) at the timepoint comprises a sinusoidal function sin( ) such that f(t) is defined as f(t)=A sin(Pt−T)+M, in which A is the amplitude A of the instantaneous heart rate data within the time window, P is the angular frequency P of breathing within the time window, T is a time displacement, and M is a mean value M of the instantaneous heart rate data within the time window. A sinusoidal function is able to represent the variation of the instantaneous heart rate well and is readily computed with digital means.

In an embodiment, the periodic biofeedback function f(t) at the timepoint comprises a skewed sinusoidal function sksin( ) such that f(t) is defined as f(t)=A sksin(Pt−T)+M=A sin[(Pt−T)+k*sin(Pt−T)], in which A is the amplitude A of the instantaneous heart rate data within the time window, P is the angular frequency P of breathing within the time window, T is a time displacement, k is a skew factor, * is a multiplication operator, and M is a mean value M of the instantaneous heart rate data within the time window. A skewed sinusoidal function is also able to take into account better the asymmetry of the inhale-exhale cycle of breathing and related heart rate variation as inhalation is often shorter than exhalation.

In an embodiment, the data processing system is configured to analyse the heart rate measurement data for each heartbeat measured with the heart rate sensor. This provides the most accurate set of data into which the periodic biofeedback function may be fitted.

In an embodiment, the data processing system is arranged to determine the resonance score based on the amplitude A of the periodic biofeedback function and the cumulative difference E within the time window, or based on the division of the amplitude A of the periodic biofeedback function by an average cumulative difference $E_{AVE}$ within the time window, or based on a tabulated and predetermined set of values for the resonance score. The tabulated and predetermined set of values for resonance score are arranged based on the amplitude A of the periodic biofeedback function and the cumulative difference E within the time window. A resonance score is an advantageous, systematic measure to indicate how well the fitting is achieved and how high amplitude in the heart rate variability is reached. A good fitting with a high amplitude, implying high heart rate variability, and small cumulative difference is indicative of strong vagus nerve stimulation. In an embodiment, in the controlled mode the breathing pacer is configured to time the breathing events to the person visually, or audially, or haptically, or any by combination thereof. These are advantageous ways in delivering the correct times of timed breathing to the person whose health is being monitored. In an embodiment, in the variable mode the breathing pacer is configured to present information based on the resonance score to the person visually, or audially, or haptically, or any combination thereof. These are advantageous ways in delivering information on how well the breathing stimulates the vagus nerve.

The breathing pacer is configured to time and indicate the breathing frequency to the person visually, or audially, or haptically, or any by combination thereof.

In the controlled mode the breathing pacer is arranged to operate at a predetermined breathing frequency. Accordingly, in the controlled mode the breathing pacer is configured operate at the predetermined breathing frequency and indicate the breathing events to the person visually, or audially, or haptically, or any by combination thereof at the predetermined breathing frequency.

In the controlled mode the system is configured to operate the breathing pacer at the predetermined breathing frequency.

In some embodiments, the predetermined breathing frequency is between 3 to 8 breaths per minute in the controlled mode.

In some further embodiments, the predetermined breathing frequency is between 4 to 7 breaths per minute in the controlled mode.

The predetermined breathing frequency being determined individually to each user such that the predetermined breathing frequency strongly stimulates the vagus nerve of the person.

In some embodiments, in the variable mode the breathing pacer is arranged to follow the breathing of the person.

Thus, in the variable mode the system is configured to determine the breathing frequency of the person based on the received heart rate measurement data. Alternatively, in the variable mode the system is configured to determine the breathing frequency of the person at the time point based on the received heart rate measurement data. Further alternatively, in the variable mode the system is configured to determine the breathing frequency of the person based on the instantaneous heart rate at the time point.

In the variable mode, the breathing pacer is configured to indicate the determined breathing frequency to the person visually, or audially, or haptically, or any by combination thereof at the predetermined breathing frequency.

In some embodiments, the system is configured to determine the breathing frequency of the person from angular frequency of the instantaneous heart rate data.

In some embodiments, the system is configured to determine measured breathing frequency of the person from the angular frequency through relation fB=P/2Π.

In some alternative embodiments, the system is configured to determine the angular frequency of the periodic biofeedback function at the timepoint such that the data processing system is arranged to determine a cycle time of the instantaneous heart rate data within a time window and determine the angular frequency of the periodic biofeedback function at the timepoint based on the cycle time.

In an embodiment, the breathing pacer comprises third software means executable on a mobile computing device, and the third software means are functionally connectable with the data processing system, and the third software means comprises computer-executable instructions for operating the breathing pacer in the controlled mode, the controlled mode comprising timing the breathing events to the person, and in the variable mode, the variable mode comprising indicating information related to a resonance score RS to the person. A mobile computing device like a smartphone or a tablet computer is an advantageous unit for implementing the functionality of the breathing pacer.

In an embodiment, in the controlled mode, the breathing pacer is arranged to time the breathing event to the person by indicating to the person a start of an inhalation of each breathing cycle; or an end of an inhalation of each breathing cycle; or a start of an exhalation of each breathing cycle; or an end of an exhalation of each breathing cycle; or any combination thereof. Many points in the breathing cycle may be advantageous when instructing the person to breathe in an externally timed fashion.

In an embodiment, the data processing system comprises first software means executable on a mobile computing device, the first software means being functionally connectable with the heart rate sensor, and the first software means comprises computer-executable instructions to receive the heart rate measurement data, analyse the heart rate measurement data, and arrange the breathing pacer into the controlled mode, and arrange the breathing pacer into the variable mode. A mobile computing device like a smartphone or a tablet computer is an advantageous unit for implementing the functionality of data processing system.

In an embodiment, the data processing system comprises second software means executable on a network data server, the first software means and the second software means are configured to exchange data over a network connection, and the second software means comprises computer-executable instructions to receive the heart rate measurement data, analyse the heart rate measurement data, arrange the breathing pacer into the controlled mode, and arrange the breathing pacer into the variable mode.

A data server, for example implemented in a cloud network server or a server cluster is an advantageous unit for analysing the heart rate measurements with a suitably fast network connection, e.g. a WLAN or a 3GPP connection.

In an embodiment, the second software means comprises computer-executable instructions for displaying information based on the parameters of the periodic biofeedback function and the cumulative difference E. A data server can provide output functionality of the analysis results e.g. through a personal webpage or an applet of a mobile computing unit like smartphone.

The present invention is based on an idea of providing a method for monitoring health of a person during a health monitoring session is disclosed. The method comprises providing a predetermined success threshold ET, measuring heart beats of the person for providing heart rate measurement data with a heart rate sensor, and indicating breathing information to the person with a breathing pacer by operating the breathing pacer: in a controlled mode, the controlled mode comprising timing breathing events to the person, and in a variable mode, the variable mode comprising indicating information related to a resonance score RS to the person. The method also comprises receiving the heart rate measurement data from the heart rate sensor into a data processing system, and analysing the heart rate measurement data in the data processing system by

- calculating instantaneous heart rate data comprising heart rate of each measured heartbeat, calculating performed over a time window in the health monitoring session, the time window comprising a timepoint, the instantaneous the heart rate data being calculated based on the heart rate measurement data received from the heart rate sensor,
- providing a periodic biofeedback function comprising parameters, the parameters comprising an amplitude A, the periodic biofeedback function comprising a cumulative difference E relative to the instantaneous heart rate data,
- fitting the periodic biofeedback function into the instantaneous heart rate data within the time window to determine the parameters of the periodic biofeedback function at the timepoint, the cumulative difference E at the timepoint, and the resonance score RS at the timepoint from the parameters and from the cumulative difference E. The method comprises also arranging the breathing pacer to operate in the controlled mode to the time the breathing events to the person, if the resonance score RS does not meet the predetermined success threshold ET, the resonance score RS determined by receiving and analysing the heart rate measurement data. The method comprises also arranging the breathing pacer to operate in the variable mode if the resonance score RS meets the predetermined success threshold ET, the resonance score RS determined by receiving and analysing the heart rate measurement data.

Advantage of the method is that a breathing frequency of the person that strongly stimulates the vagus nerve is determined quickly when compared to prior art systems, without complex arrangements in the respiratory tract or with long datasets needed by spectral analysis by Fourier transforms. With the controlled mode, a good breathing frequency range for vagus nerve stimulation (indicated e.g. by a high resonance score) is found fast, and then with the variable mode, the person may experiment further if even an optimal breathing frequency is found, indicated e.g. by a very high resonance score.

In an embodiment, in the fitting the method comprises determining the cumulative difference E between the instantaneous heart rate data and the periodic biofeedback function within the time window, the time window comprising the timepoint, and performing the fitting based on a calculated minimum of the cumulative difference E within the time window to determine the parameters of the periodic biofeedback function at the timepoint, the time window comprising the timepoint. Fitting a periodic function (here, the periodic biofeedback function) to a measurement data (here, to instantaneous heart rate data) based on a minimum of a cumulative difference is an effective way to achieve the fitting.

Accordingly, in the method comprises arranging the breathing pacer into the controlled mode based on the analyzing of the heart rate measurement data.

Further, the method comprises comparing the determined resonance score RS at the time point to the predetermined success threshold ET and arranging the breathing pacer into the controlled mode if the resonance score RS does not meet the predetermined success threshold ET based on the comparing.

Accordingly, the method comprises arranging the breathing pacer into the variable mode based on the analyzing the heart rate measurement data.

Further, the method comprises comparing the determined resonance score RS at the time point to the predetermined success threshold ET and arranging the breathing into the variable mode if the resonance score RS meets the predetermined success threshold ET based on the comparing.

In some embodiments and according to the above, the method comprises actively changing between the controlled mode and the variable mode based on the determined resonance score and the predetermined success threshold ET.

In an embodiment, the fitting is performed with a least squares method; or a modified least squares method; or a random search; or an exhaustive search; or any combination thereof. These fitting methods are effective methods for the fitting and they may be used in combination to avoid the convergence of the fitting method to a local minimum of the cumulative difference instead of a global minimum.

In an embodiment, the periodic biofeedback function f(t) at the timepoint comprises a sinusoidal function sin( ) such that f(t) is defined as f(t)=A sin(Pt−T)+M, in which A is the amplitude A of the instantaneous heart rate data within the time window, P is the angular frequency P of breathing within the time window, T is a time displacement, and M is a mean value M of the instantaneous heart rate data within the time window. A sinusoidal function is able to represent the variation of the instantaneous heart rate well and is readily computed with digital means.

In an embodiment, the periodic biofeedback function f(t) at the timepoint comprises a skewed sinusoidal function sksin( ) such that f(t) is defined as f(t)=A sksin(Pt−T)+M=A sin [(Pt−T)+k*sin(Pt−T)], in which A is the amplitude A of the instantaneous heart rate data within the time window, P is the angular frequency P of breathing within the time window, T is a time displacement, k is a skew factor, * is a multiplication operator, and M is a mean value M of the instantaneous heart rate data within the time window. A skewed sinusoidal function is also able to take into account the asymmetry of the inhale-exhale cycle of breathing and related heart rate variation as inhalation is often shorter than exhalation.

In an embodiment, the method comprises determining the resonance score based on the amplitude A of the periodic biofeedback function and cumulative difference E within the time window, or based on the division of the amplitude A of the periodic biofeedback function by the average cumulative difference $E_{AVE}$ within the time window, or based on a tabulated and predetermined set of values for resonance score the tabulated and predetermined set of values for resonance score arranged based on the amplitude A of the periodic biofeedback function and the cumulative difference E within the time window. The resonance score is an advantageous, systematic measure to indicate how well the fitting is achieved and how high amplitude is reached. A good fitting with a high amplitude and small cumulative difference is indicative of strong vagus nerve stimulation.

In an embodiment, when operating the breathing pacer in the controlled mode, the controlled mode comprises timing the breathing events to the person visually, or audially or, haptically or any combination thereof. These are advantageous ways in delivering the correct times of timed breathing to the person whose health is being monitored.

In an embodiment, when operating the breathing pacer in the variable mode, the variable mode comprises indicating information related to a resonance score RS to the person visually, or audially, or haptically, or any combination thereof. These are advantageous ways in delivering information on how well the breathing stimulates the vagus nerve.

In the method, the breathing pacer times and indicates the breathing frequency to the person visually, or audially, or haptically, or any by combination thereof.

In the controlled mode the breathing pacer operates at a predetermined breathing frequency. Accordingly, in the controlled mode the breathing pacer operates at the predetermined breathing frequency and indicates the breathing events to the person visually, or audially, or haptically, or any by combination thereof at the predetermined breathing frequency.

In the controlled mode the breathing pacer operates at the predetermined breathing frequency.

In some embodiments, the predetermined breathing frequency is between 3 to 8 breaths per minute in the controlled mode.

In some further embodiments, the predetermined breathing frequency is between 4 to 7 breaths per minute in the controlled mode.

The predetermined breathing frequency is determined individually to each user such that the predetermined breathing frequency strongly stimulates the vagus nerve of the person.

In some embodiments, in the variable mode the breathing pacer follows the breathing of the person.

Thus, in the variable mode the method comprises determining the breathing frequency of the person based on the received heart rate measurement data. Alternatively, in the variable mode the method comprises determining the breathing frequency of the person at the time point based on the received heart rate measurement data. Further alternatively, in the variable mode the method comprises determining the breathing frequency of the person based on the instantaneous heart rate at the time point.

In the variable mode, the breathing pacer indicates the determined breathing frequency to the person visually, or audially, or haptically, or any by combination thereof at the predetermined breathing frequency.

In some embodiments, the method comprises determining the breathing frequency of the person from angular frequency of the instantaneous heart rate data.

In some embodiments, the method comprises determining measured breathing frequency of the person from the angular frequency through relation fB=P/2Π.

In some alternative embodiments, the method comprises determining the angular frequency of the periodic biofeedback function at the timepoint such that the data processing system is arranged to determine a cycle time of the instantaneous heart rate data within a time window and determine the angular frequency of the periodic biofeedback function at the timepoint based on the cycle time.

In an embodiment, the method is executed in a system according to the system aspect or its embodiments as defined above. The system is an advantageous and dedicated system to execute the method.

As an aspect of the present invention, a computer program is disclosed. The computer program comprises executable instructions which are configured to execute all the steps of a method as defined above in the method aspect and its embodiments a computer, or a mobile computing device, or network data server, or any combination thereof.

The invention is based on the idea on informing the person whose health is being monitored about heart rate variability and related information that may be indicative of an improved vagus nerve stimulation through breathing. When a breathing rate that may indicate an increased stimulus is detected through the heart rate variation, the user is allowed to experiment, with the variable mode of the breathing pacer, with slightly different breathing rates and with different inhalation styles, for example in terms on depth of the inhalation or symmetry (in duration) of the inhalations and exhalations (asymmetry being manifested for example by a longer exhalation than inhalation). Strong vagus nerve stimulation through breathing may be indicated by a measured heart rate variation that becomes periodic, has a steady and high amplitude and alternates around a mean. By fitting a periodic biofeedback function, for example a time dependent sinusoidal function with an amplitude, angular frequency, phase and offset (mean) value, a quick determination on the level of vagus nerve stimulation through breathing is achieved. In the optimal breathing frequency, the amplitude of the variation is maximal and the error between the fitted periodic biofeedback function and the measured data is minimal, indicating a strong periodicity and variability in the heart rate variability that may indicate a strong vagus nerve stimulation.

The invention has many advantages. Information on a good or even optimal breathing rate for vagus nerve stimulus through breathing can be determined without any invasive procedures or electrical stimulation. Breathing measurements in, from or by the respiratory tract are also not needed. Instead, mere heart rate measurements of individual heartbeats are sufficient. Heart rate measurements are very convenient with modern technologies.

With the fitting of the periodic biofeedback function on instantaneous heart rate data, a very quick determination of the relevant parameters of the function is also achieved as the data does not have to be subjected to complex spectral analyses like Fourier transforms that may require very long samples of heartbeat information to become reliable. With the invention, information on the heart rate variation and consequently the indication on how well the breathing rates suits the vagus nerve stimulation may become available within five to ten seconds. This is considerably faster than with prior art systems or methods.

It is to be noted that the presented invention does not disclose a diagnostic or therapeutic invention. To be a diagnostic invention, there would need to be one or more "normal" ranges of heart rate variabilities, and then one or more "abnormal" ranges of heart rate variabilities, and, then according to the invention, a determination and diagnostics should be reached based on the measured heart rate variability, and the normal and abnormal ranges. However, the present invention is not aimed into such determination.

Similarly, to be a therapeutic invention, the invention (system or method) should directly have a therapeutic effect. However, it is the breathing of the person that may stimulate the vagus nerve to a varying degree, and the strength of the stimulus may be dependent on the correct breathing rate. However, the invention lets the user to monitor the effect of the breathing to the heart rate variability. High heart rate variability may have health benefits and it may be indicative of improved vagus nerve stimulation, achieved through "correct" breathing. Thus, the invention allows monitoring of the person, and it is up to the user to perform the breathing through the results of the monitoring. The breathing with a certain breathing rate may then have health related positive effects.

For the purposes of this text, "vagus nerve stimulation" means "vagus nerve stimulation through breathing" that may be guided and observed by the system, method and computer program, as the system, method or computer program disclosed in the present text do not, in any way, directly stimulate the body of the person.

BRIEF DESCRIPTION OF THE DRAWINGS

The invention is described in detail by means of specific embodiments with reference to the enclosed drawings, in which.

DETAILED DESCRIPTION OF THE INVENTION

In the Figures and in this text, like numbers (for example 112) and like labels (for example 112*m*) relate to like elements.

Figure 1:
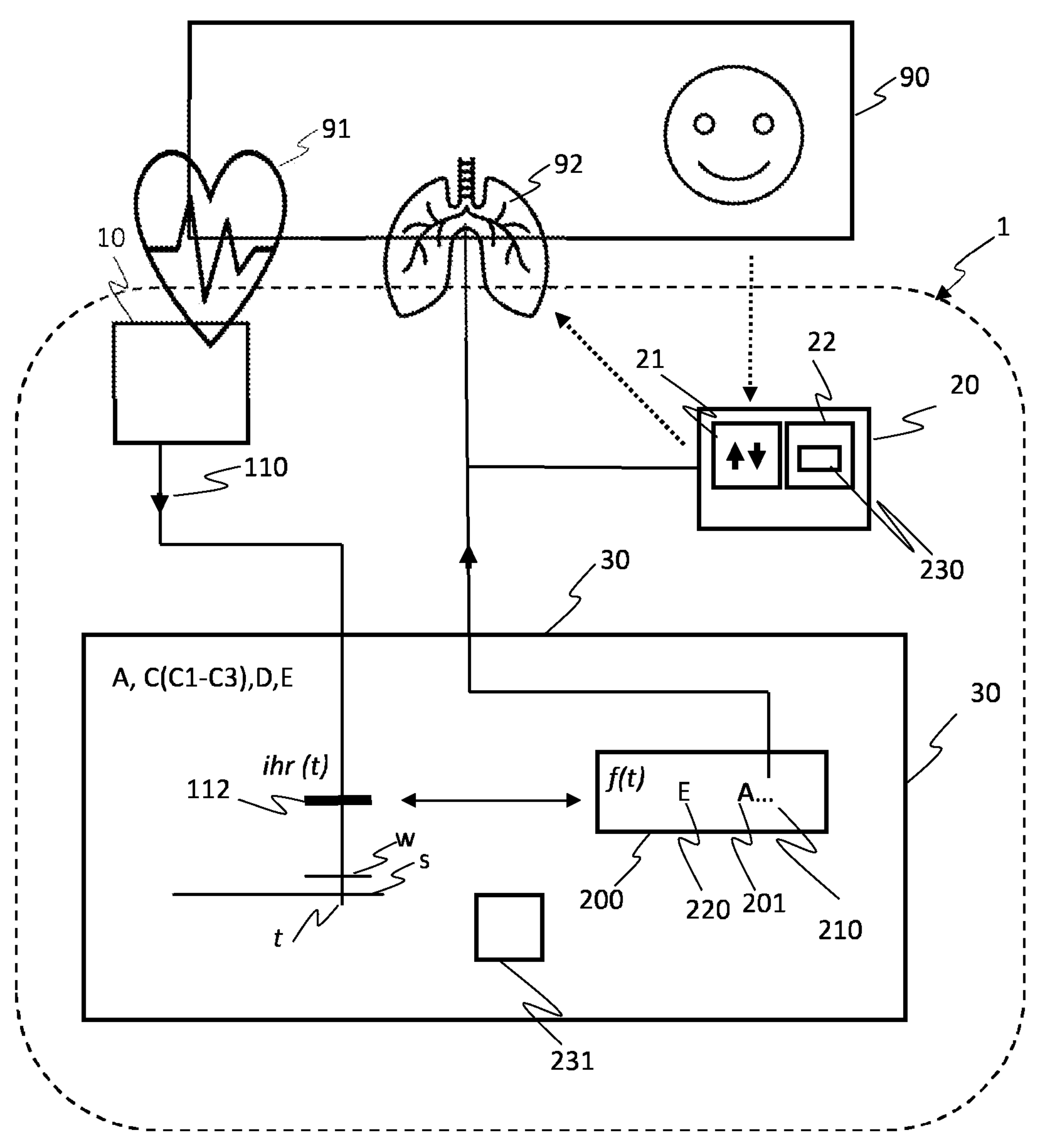
FIG. 1 shows schematically an embodiment of the system and the person being monitored.

FIG. 1 shows schematically an aspect of the present invention, a system 1 for monitoring health of a person 90 during a health monitoring session s. The monitoring is performed by analysing heart rate of the person and by guiding the person to breathe so that the heart rate indicates a strong vagus nerve stimulation. Determining the personal breathing rate that optimally stimulates the vagus nerve is a relevant technical problem in the fitness and medical community and subject to a growing interest in the field.

For the purposes of this text, a health monitoring session s is any period of time during which the person is interested in observing his/her physiological matters related for example to breathing, cardiac activity or state of the nervous system, and in particular the interest of the person may be in the optimal vagus nerve stimulation through breathing. Thus, in the context of the present application, breathing exercises, heart rate measurements and producing information related to vagus nerve stimulation are called "health monitoring" of a person, and heart rate measurements and vagus nerve stimulation are carried out during a health monitoring session. A health monitoring session may comprise a breathing exercise during which the person tries to achieve good or even optimal vagus never stimulation through breathing.

For the purposes of this text, the terms "breathing rate" and "breathing frequency" are used interchangeably, and they all relate to a time-dependent breathing frequency of a person, calculated for example from the inverse of timespan of start of two subsequent inhalations when a person breathes. Usually breathing frequency is expressed in breathes per one minute (60 seconds), and it is usually 3-8 breaths/minute for an adult person in rest, especially when the person attempts strong or optimal vagus nerve stimulation through breathing.

For the purposes of this text, "within the time window w" means a period of time that starts and ends in the time window w, but does not necessarily span the entire time window w.

For the purposes of this text, the "instantaneous heart rate" $f_1$ may be defined as the inverse of the interval (in time) of two consecutive heartbeats $T_{R\text{-}R}$, and usually this heart rate is expressed as a frequency in minutes. The interval may be measured, for example, as the interval between timepoint of two consecutive R waves in the so-called QRS complex of a beating human heart. Thus, stated exactly, $f_1=60/T_{R\text{-}R}$, implying that an instantaneous heart rate of 60 beats in one minute ("BPM", beats per minute) means that the interval between two consecutive R waves of a beating heart is 1s. Instantaneous heart rate varies from one heartbeat to the next, and this variation is called, in general, heart rate variability. Instantaneous heart rate usually varies periodically and around a mean. For example, mean of an instantaneous heart rate mean may be 70 beats in one minute, and the instantaneous heart rate may vary with an amplitude of 8 beats/minute around the mean such that minimum instantaneous heart rate is 62 beats/minute and maximum 78 beats/minute over a period of time when the person is at rest. Especially breathing, as is discussed in the present text, has the ability to alter the instantaneous heart rate.

The system 1 comprises a heart rate sensor 10 which is arranged to measure heart beats of the person 90 for providing heart rate measurement data 110. Heart of the person is indicated with symbol 91, and breathing information is associated with symbol of lungs 92. Several kinds of heart rate sensors exist, for example electrocardiographic sensors that measure the electrical activity of heart and comprise usually an elastic band or belt worn around the chest area of a person 90, and photoplethysmographic sensors that detect the heart rate based on variations of optical properties of tissue and which comprise for example a clip with a sensor worn in an earlobe or a finger of a person 90.

The system also comprises a breathing pacer 20 configured to indicate breathing information to the person 90. The breathing pacer 20 may be a device, or a utility, application or a computer program arranged in for example in a mobile computing device like a smartphone or a tablet computer that is configured to guide the person to reach a breathing rate, or more generally a breathing style, that optimizes the vagus nerve stimulation through breathing.

The breathing pacer 20 is arranged to operate in a controlled mode 21. The controlled mode 21 comprises timing breathing events to the person 90. In other words, in the controlled mode 21, the breathing pacer 20 is arranged to time the breathing events to the person 90. For the purposes of this text, "timing breathing events" means that the breathing pacer 20 signals or is arranged to signal to the person the moment in time the person should breathe, for example, start the next inhalation. The system 1 may be arranged to adjust the instructed breathing rate with which the timing is performed to the person 90. The breathing pacer is arranged to operate in the controlled mode when the heart rate data indicates that the vagus nerve stimulation is not very strong.

The breathing pacer 20 may comprise digital electronics, memory or memories, power unit like a battery, ASICs, FPGAs, digital busses, microcontrollers and microprocessors to arrange its various operations. The breathing pacer 20 may also comprise one or more input devices like a keyboard, a microphone or a touch screen display, and output devices like a LED, a display, a loudspeaker or a haptic device like a linear resonant actuator.

The breathing pacer is also arranged to operate in a variable mode 22. The variable mode 22 comprises indicating information related to a resonance score RS 230 to the person 90. In other words, in the variable mode 22, the breathing pacer 20 is arranged to indicate information related to a resonance score RS 230 to the person 90. The breathing pacer 20 operates or is arranged to operate in the variable mode when the heart rate data indicates that the vagus nerve stimulation is strong enough to let the person 90 to experiment with the breathing rate autonomously without the direct, controlled timing of breathing and timing of breathing events arranged with the breathing pacer 20.

Information related to a resonance score 230 may be any information of the health effects of the health monitoring session s and of the breathing that may be derived from the resonance score. Thus, the information related to a resonance score may be the resonance score 230 directly, or it may be another indication of the effectivity of the breathing in vagus nerve stimulation that is based on the resonance score 230. For example, information related to a resonance score may be a displayed message to the person in text format in the breathing pacer 20 indicating the vagus nerve stimulation effectivity, based on the resonance score 230. Examples of such texts are "excellent vagus nerve stimulation", "good vagus nerve stimulation" and "only weak vagus nerve stimulation".

The system 1 comprises also a data processing system 30 which is configured (as operation A) to receive the heart rate measurement data 110 from the heart rate sensor 10 during the health monitoring session s. This data may be transmitted for example in digital or analogue voltage signals for example with electrical connections from the heart rate sensor 10 to the data processing system 30.

The data processing system 30 is also arranged to provide a predetermined success threshold ET 231. The predetermined success threshold ET 231 is a measure on how strong the vagus nerve stimulus should be to switch the operation of the breathing pacer 20 from the controlled mode to the variable mode. The predetermined success threshold 231 will be defined in more detail below.

The data processing system 30 is also (as operation C) configured to analyse the heart rate measurement data 110.

In the analysis (operation C), the data processing system 30 is configured to (as operation C1) calculate instantaneous heart rate data 112 comprising the instantaneous heart rate of each measured heartbeat. The instantaneous heart rate data $f_1$ 112 may be defined as the inverse of the interval (in time) of two consecutive heartbeats, as defined already above. The instantaneous heart rate data 112 is calculated based on the heart rate measurement data 110 received from the heart rate sensor 10. This is done over a time window w in the health monitoring session s. The time window w comprises a timepoint t. As an example, time window w might start at timepoint 1500*s* (measured from an arbitrary point in time) and end at timepoint 1540*s*, (making the time window 40*s* wide) and timepoint t can be the midmost timepoint at 1520*s*. In a practical implementation, the time window w may comprise discrete timepoints, for example 10, 20 or 40 discrete timepoints where the instantaneous heart rate data 112 is represented for example by digital computing means. The heath monitoring session s may comprise many, possibly overlapping time windows w.

Figure 2:
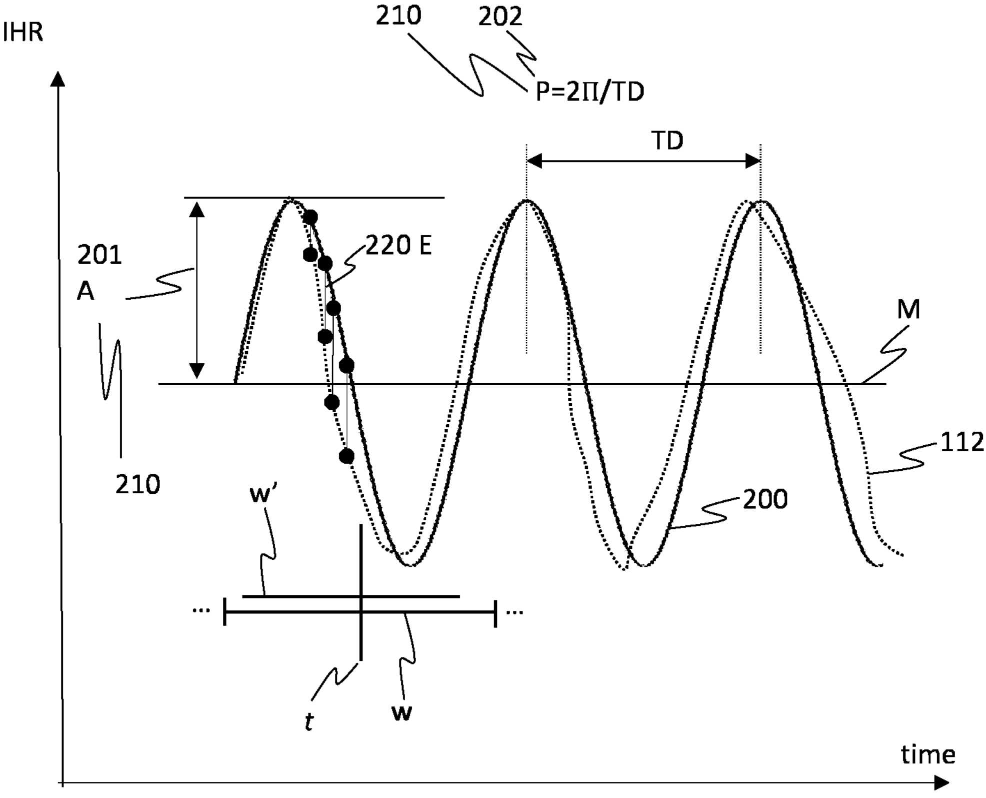
FIG. 2 shows concepts related to an embodiment of a periodic biofeedback function.

Next, referring to FIG. 2, in the analysis, the data processing system 30 (as operation C2) is configured to provide a periodic biofeedback function 200, which comprises parameters 210. The parameters 210 comprise an amplitude A 201 of the periodic biofeedback function 200. In FIG. 2, the periodic biofeedback function is shown with a solid line 200, and the instantaneous heart rate data 112 as the dotted line over a time axis t. The periodic biofeedback function 200 comprises also a cumulative difference E 220 relative to the instantaneous heart rate data 112. In FIG. 2, the cumulative difference E 220 may be the difference between the curves 200 and 112 in an arbitrary time interval w' within the time window w. The arbitrary time interval w' may be within the time window w completely or partially. As shown in FIG. 2, the instantaneous heart rate data 112 (IHR as the y axis) approximately oscillates around an approximate mean M, with an approximate amplitude A and with an approximate angular frequency P, and the values for the parameters A, P and M may be found by arranging the data processing system 30 to the fit the periodic biofeedback function 200 to the instantaneous heart rate data 112. Mean M may be for example 65 beats per minute (BPM), and the amplitude A may be 5 BPM.

In the analysis, the data processing system 30 (as operation C3) is also configured to fit the periodic biofeedback function 200 into the instantaneous heart rate data 112 within time window w to determine the parameters 210 of the periodic biofeedback function 200 at the timepoint t, to determine the cumulative difference E 220 at the timepoint t, and to determine the resonance score RS 230 at the timepoint t from the parameters 210 and from the cumulative difference E 220, both the parameters 210 and the cumulative difference E 220 at the timepoint t.

Referring back to FIG. 1, The data processing system 30 is also configured, as operation D) to arrange the breathing pacer 20 into the controlled mode 21 to time the breathing events to the person 90 if the resonance score RS 230 does not meet the predetermined success threshold ET 231, the resonance score RS 230 meaning here the resonance score RS 230 at the timepoint t. The resonance score RS 230 is determined by receiving (operation A) and analysing (operation C) the heart rate measurement data 110.

In the controlled mode, the breathing pacer 20 is configured to assist the person to find an optimal breathing rate, and more generally, breathing style by indicating the moments of time for the breathing. For example, to time the breathing, the breathing pacer may be arranged to indicate the start of the inhalation the person should take (take a breath in). As another example, the breathing pacer may also be arranged to indicate the start of the exhalation the person should let out. Indication may be arranged e.g. by a beep from a loudspeaker of a breathing pacer 20 or by an emergent symbol on a display of the breathing pacer 20.

In the controlled mode D, the data processing system 30 may be arranged to control the breathing pacer 20 to change the breathing rate with which the breathing pacer 20 times the breathing events to the person 90 to assist the person to find an optimal breathing rate. Thus, in the controlled mode, the data processing system 30 is arranged to control the breathing pacer 20 such that several breathing rates may be tried by the person 90, by altering the timing of the breathing events to the person 90. For the several breathing rates, different results are obtained as parameters 210 of the periodic biofeedback function 200, as cumulative difference 220, and as the resonance score 230 through the process of operations A and C1-C3 as defined above.

By guiding the person 90 with the breathing pacer 20 so that the person 90 may find the optimal breathing rate, reaching strong vagus nerve stimulation is faster than with a random method as usually the person does not have recollections of the rhythm and ways he/she has breathed just awhile ago, and iterating and finding the personal breathing rate needed for a strong vagus nerve stimulation without outside help provided by the system 1 and the breathing pacer 20 is thus often challenging.

The data processing system 30 is also configured to arrange the breathing pacer 20 into the variable mode 22 (operation E) if the resonance score RS 230 meets the predetermined success threshold ET 231, the resonance score RS 230 meaning here the resonance score RS 230 at the timepoint t. The resonance score RS 230 is determined by receiving (operation A) and analysing (operation C) the heart rate measurement data 110. In a variable mode, the breathing pacer is arranged to indicate information related to the resonance score 230 to the person. The resonance score 230 may indicate how optimal the vagus nerve stimulation is. For example, the resonance score 230 may be high, indicating strong vagus nerve stimulation, when the amplitude A 201 of the periodic biofeedback function 200 is high, and the cumulative difference E 220 is low. Similarly, the resonance score 230 may be low, indicating poor vagus nerve stimulation, when the amplitude A 201 of the periodic biofeedback function 200 is low, and the cumulative difference E 220 is high.

If the breathing pacer 20 is arranged to operate in the variable mode 22 and if the resonance score 230 no longer meets the success threshold ET 231 (for example, the resonance score 230 becomes "too low"), the data processing system 30 is configured to arrange the breathing pacer 20 back to the controlled mode (and to continue operation D). Similarly, if the breathing pacer 20 is arranged to operate in the controlled mode 21 and if the resonance score 230 meets the success threshold ET 231 (for example, the resonance score 230 becomes "high enough"), the data processing system 30 is configured to arrange the breathing pacer 20 back to the variable mode (and to continue operation E).

Thus, with the system 1, determining the optimal vagus nerve stimulation is achieved with no complex and inconvenient measurements for example in the respiratory tract, and also quickly, as long sample periods needed by a Fourier transform and related spectral analysis are not needed. With the controlled mode, a good breathing rate can be "iterated" fast for a good vagus nerve stimulation, and once it is found, with the variable mode, the breathing rate, and in general, breathing style, can be "fine tuned" to an optimal state to reach maximal vagus nerve stimulation.

The data processing system 30 may be arranged to repeat the operations mentioned above for the duration of the health monitoring session s, for a plurality of time windows w. Thus, the health monitoring session s may comprise a plurality of time windows w, each comprising a timepoint t.

In other words, the data processing system 30 may be arranged to repeat operations A, C (C1-C3), D and E for the duration of the health monitoring session s, for a plurality of time windows w to find the optimal breathing rate that optimally stimulates the vagus nerve.

Figure 3:
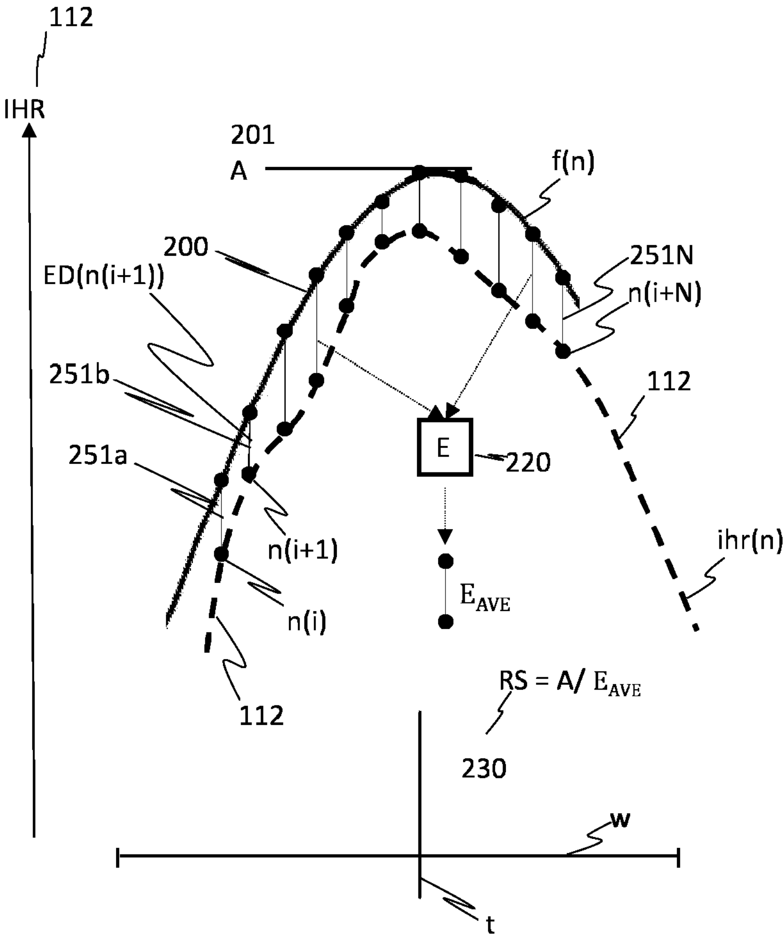
FIG. 3 shows details of a fitting process between the periodic biofeedback function and the instantaneous heart rate data.

In an embodiment, referring to FIG. 3, in the fitting (the operation C3), the data processing system 30 is configured to determine the cumulative difference E, indicated with symbol 220 between the instantaneous heart rate data 112 and the periodic biofeedback function 200 within the time window w comprising the timepoint t. The data processing system 30 is also configured perform the fitting based on a calculated minimum of the cumulative difference E 220 within the time window w to determine the parameters 210 of the periodic biofeedback function 200 at the timepoint t. In other words, the time window w comprises the timepoint t.

After the fitting (the operation C3), the data processing system 30 may also be configured determine the cumulative difference E 220 at the timepoint t from the calculated minimum of the cumulative difference E 220 within the time window w.

After the fitting (the operation C3), the data processing system 30 may also be configured to set the value of the cumulative difference E 220 at the timepoint t to the value of the calculated minimum of the cumulative difference E 220 within the time window w. In other words, after the fitting, the cumulative difference E 220 may have a minimum value within the time window w.

The concept of the cumulative difference E is illustrated further in FIG. 3, where the instantaneous heart rate data 112 is show as a curve 112. Instantaneous heart rate data 112 comprises discrete instantaneous heart rate values at discrete points in time (three discrete points shown, n(i), n(i+1), and n(i+N)) within the time window w, the time window w comprising the timepoint t. The discrete points in time may comprise the timepoint t. For each discrete point in time, a discrete difference ED (three discrete differences labelled in FIG. 3, marked with 251*a*, 251*b*, 251N) is determined that contributes to the cumulative difference E 220. The discrete differences (251*a*, 251*b*, 251N) may be determined as the subtraction of the values of the instantaneous heart rate data 112 (represented by function ihr(n)) at the corresponding discrete timepoint n(i) . . . n(i+N), and the values of the periodic biofeedback function 200 f(n) in the discrete timepoint n(i) . . . n(i+N), where . . . denotes "from n(i) to n(i+N)". In other words, ED(n)=ihr(n)−f(n).

In an embodiment, the data processing system 30 may be arranged to calculate the cumulative difference E 220 as the sum of absolute values of the discrete differences (251*a*-251N) between values of the instantaneous heart rate data 112 and values of the periodic biofeedback function 200 at the discrete timepoints n(i) . . . n(i+N), $$E(t) = \sum_{j=i}^{N+i} |ihr(n(j)) - f(n(j))|$$

where the | | denotes the absolute value and tis a timepoint within the discrete datapoints n(j).

As another embodiment, the data processing system 30 may be arranged to calculate the cumulative difference E 220 as the sum of squared values of the discrete differences (251*a*-251N) between values of the instantaneous heart rate data 112 and values of the periodic biofeedback function 200, wherein t is a timepoint within the discrete datapoints n(j), $$E(t) = \sum_{j=i}^{N+i} (ihr(n(j)) - f(n(j)))^2.$$

In fitting, in operation C3, the data processing system 30 may be arranged to vary the parameters 210 of the periodic biofeedback function 200, and for each set of parameters 210, determine the cumulative difference E 220 within a time window w. In fitting, in operation C3, the data processing system 30 may be also arranged determine the calculated minimum of the cumulative difference E 220, and the parameters 210 of periodic biofeedback function 200 used to reach the minimum cumulative difference 220 within a time window w. To determine the calculated minimum of the cumulative difference E 220, the data processing system 30 is arranged to vary of the parameters 210 of the periodic biofeedback function 200 for a number of iteration loops. The data processing system 30 is arranged to base the variation of the parameters 210 to one or more search algorithms or fitting methods. The data processing system 30 is then configured to determine the parameters 210 resulting in a calculated minimum of the cumulative difference 220, the parameters 210 resulting in a calculated minimum of the cumulative difference 220 providing the result of the fitting, that is, for example providing the values of the parameters 210 of the periodic biofeedback function 200 and the cumulative difference E 220.

The data processing system 30 may be arranged to base the varying of the parameters 210 of the periodic biofeedback function 200 to determine the calculated minimum of the cumulative difference E 220 on various search algorithms or "fitting methods" like a least squares method, a modified least squares method, a random search method or an exhaustive search method. The data processing system 30 may be also arranged to use any combination of the search algorithms or fitting methods of the least squares method, the modified least squares method, the random search method or the exhaustive search method to determine the calculated minimum of the cumulative difference E 220, and thus the parameters 210 of the periodic biofeedback function 200 resulting in the calculated minimum of the cumulative difference E 220. In other words, the data processing system may be configured perform the fitting (operation C3) within the time window w with a least squares method, or a modified least squares method, or a random search, or an exhaustive search, or any combination thereof.

With the random search method, the data processing system 30 is arranged to vary the parameters 210 of the periodic biofeedback function 200 randomly such that the values of the parameters 210, within ranges of feasible values, are arranged to be randomly assigned during the iteration loops. The data processing system 30 is then arranged to choose the set of parameters 210 reaching the calculated minimum of the cumulative difference 220 as the parameters 210 of the periodic biofeedback function 200. The data processing system 30 may also be arranged to start the random assignment of parameters from an initial guess of one or more of the parameters 210.

With the exhaustive search method, the data processing system 30 is arranged to vary the parameters 210 of the periodic biofeedback function 200 such that every combination of parameters 210, within ranges of feasible values in a discrete set of the feasible values, are arranged to be tried during the iteration loops. For example, it may be determined that the maximum amplitude A 201 of the instantaneous heart rate is 20 beats/minute, and all values of A, from zero to 20 beats/minute are tried with a discrete interval of for example 0.2 beats/minute. In other words, values 0, 0.2, 0.4, . . . 20 are tried when the amplitude parameter A 201 is varied. The same process is repeated simultaneously for other parameters, providing a nested group of iteration loops, for example four nested iteration loops for four parameters 210 (amplitude A 201, angular frequency P 202, mean M 205 and phase or time displacement T of the periodic biofeedback function 200). The data processing system 30 is then arranged to choose the set of parameters 210 achieving the calculated minimum of the cumulative difference 220 as the parameters 210 of the periodic biofeedback function 200. The data processing system 30 may also be arranged to start the variation of the parameters 210 from an initial guess of one or more of the parameters 210.

With the least squares search method, the data processing system 30 is arranged to vary the parameters 210 of the periodic biofeedback function 200 based on the numerical Gauss-Newton algorithm to find the calculated minimum of the cumulative difference E 220. By representing the parameters 210 of the periodic biofeedback function with a vector B, and discrete difference between the periodic biofeedback function 201 and the instantaneous heart rate data 112 at discrete timepoint n(j) by a "residual" $r_j$ as function of the parameters ß 201 (number of parameters being k), the calculated minimum of the cumulative difference E 220 is found when sum of squares S(β) is minimized, where $$S(\beta) = \sum_{j=i}^{N+i} r_j(\beta)^2.$$

With an initial guess for the parameters 210 of $\beta^0$, the data processing system 30 is arranged to vary the parameters based on the iteration rule that may be, for example $$\beta^{L+1} = \beta^L - (J_r^T J_r)^{-1} J_r^T r(\beta^L),$$

where L is the Lth iteration loop, and J is the Jacobian matrix with elements, $$(J_r)_{jk} = \frac{\partial r_j(\beta^L)}{\partial \beta_k},$$

T denotes the matrix transpose and superscript −1 the matrix inverse.

With the modified least squares search method, the data processing system 30 is arranged to vary the parameters 210 of the periodic biofeedback function 200 based on the numerical Levenberg-Marquardt algorithm to find the calculated minimum of the cumulative difference E 220. The Levenberg-Marquardt algorithm is similar to the Gauss-Newton algorithm, but with the Levenberg-Marquardt algorithm the iteration rule may be, for example $$\beta^{L+1} = \beta^L - (J_r^T J_r - \lambda I)^{-1} J_r^T r(\beta^L),$$

where λ is a damping parameter and I is an identity matrix. The damping factor λ may be arranged by the data processing system 30 for the iteration loops to a value, based on the error of the iteration, determined by the difference of the results of two consecutive iteration loops, that configures the iteration to find the parameters 210 of the periodic biofeedback function 200 faster. If the error of the iteration increases, the data processing system 30 may be arranged to increase the damping factor. If the error of the iteration decreases, the data processing system 30 may be arranged to decrease the damping factor. Clearly, with λ=0, the Levenberg-Marquardt algorithm reduces to the Gauss-Newton algorithm.

FIG. 3 illustrates also a concept of resonance score 230 further. Optimal vagus nerve stimulation is achieved when the behaviour of the instantaneous heart rate data 112 is periodic and alternates steadily over time around a mean with a large amplitude A 201. As the instantaneous heart rate data 112 is arranged to be represented by the periodic biofeedback function 200 in the data processing system 30, the cumulative difference E 220 between the periodic biofeedback function 200 and the instantaneous heart rate data 112 may determine the impact on the vagus nerve stimulation more accurately together with amplitude A 201 than with amplitude A 201 alone. This is because the amplitude A 201 may also be large when the periodic biofeedback function 200 does not follow the instantaneous heart rate data 112 well. Thus, as a measure of the ability of the breathing to stimulate vagus nerve, the data processing system 30 may be configured to determine a resonance score 230.

For example, the resonance score RS 230 may be defined as a ratio of the amplitude 201 of the periodic biofeedback function, and an average difference $E_{AVE}$ of the cumulative difference E 220 of N discrete timepoint within the time window w, $E_{AVE}$=E/N. In other words, RS=A/$E_{AVE}$. The resonance score 230 may also be defined by a two-dimensional table of values for amplitude 201 and average difference $E_{AVE}$. The resonance score RS 230 values may be then pre-recorded for the A and $E_{AVE}$ entries in the table, for example in the data processing system 30. Generalizing, the resonance score 230 may be arranged to be determined such that a resonance score 230 based on a large value of amplitude A 201 and low value of cumulative difference E 220 indicates that the resonance score 230 meets the predetermined success threshold ET 231.

Thus, the predetermined success threshold ET 231 may be, for example, a number, and the data processing system 30 may be configured to compare the resonance score 230, which may be another number, to the predetermined success threshold ET 231 to determine, if the resonance score RS 230 meets the predetermined success threshold ET 231, or if the resonance score RS 230 does not meet the predetermined success threshold ET 231.

Figure 4:
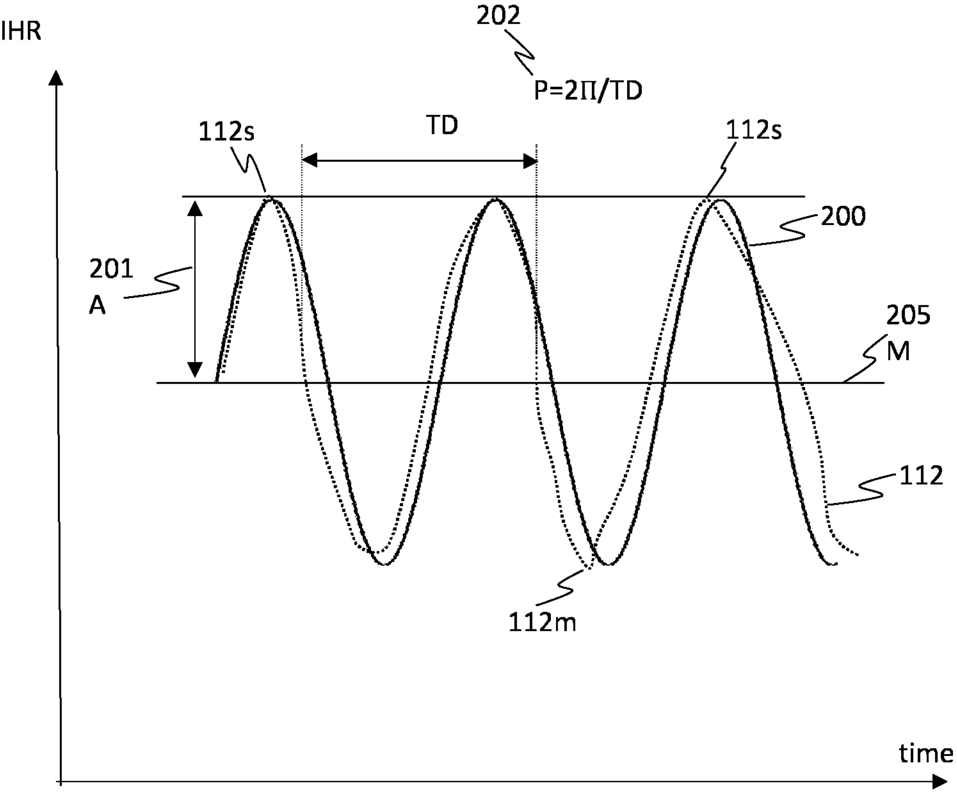
FIG. 4 shows concepts related to an embodiment of a periodic biofeedback function, the sinusoidal function.

Turning to FIG. 4, in an embodiment, in fitting and in determining the parameter indicating the amplitude A 201 of the periodic biofeedback function 200 at the timepoint t, the data processing system 30 is arranged to determine a minimum instantaneous heart rate 112*m* and a maximum instantaneous heart rate 112*s* of the instantaneous heart rate data 112 within the time window w, subtract the minimum instantaneous heart rate 112*m* from the maximum instantaneous heart rate 112*s*, divide the value of subtraction by 2, and determine the parameter indicating the amplitude A 201 of the periodic biofeedback function 200 at the timepoint t based on the value of the division. The data processing system 30 may be arranged to set the amplitude parameter A 201 to value of the division directly such that in the determination of the parameters 210, in fitting, the data processing system 30 keeps parameter indicating the amplitude A 201 of the periodic biofeedback function 200 at a value based on the value of the division.

Alternatively or additionally, the data processing system 30 may use the value of the division as an initial guess in the search algorithm or fitting method.

Still referring to FIG. 4, in an embodiment, the parameters 201 of the periodic biofeedback function 200 comprise an angular frequency P 202, and in fitting and in determining the parameter indicating the angular frequency P 202 of the periodic biofeedback function 200 at the timepoint t, the data processing system 30 is arranged to determine a cycle time TD 115 of the instantaneous heart rate data 112 within the time window w, and determine the parameter indicating the angular frequency P 202 of the periodic biofeedback function 200 at the timepoint t based on the cycle time TD 115.

Figure 5:
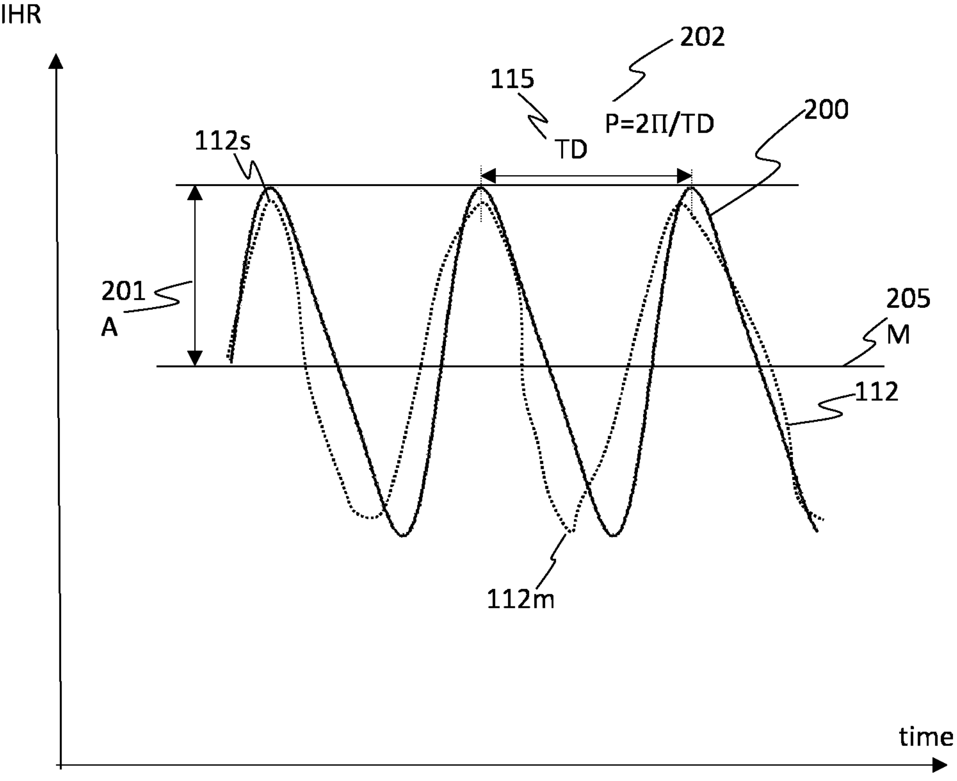
FIG. 5 shows concepts related to an embodiment of a periodic biofeedback function, a skewed sinusoidal function, FIG. 6*a* show schematically concepts related to an embodiment of the system related resonance score (FIG. 6*a*), to a so-called breathing pacer (FIG. 6*b*), and to the inhalation and exhalation cycle of a person (FIG. 6*c*).

As shown in FIG. 5, the data processing system 30 may be arranged to determine two subsequent, essentially same values (or two values that are within a margin of error) within the instantaneous heart rate data 112 and then measure the cycle time TD between two subsequent, essentially same values, and then determine the angular frequency from the known relation P=2Π/TD. The data processing system 30 may be arranged to determine the two subsequent, essentially same values (or two values that are within a margin of error) on two successive rising or falling edges of the instantaneous heart rate data 112. The data processing system 30 may be also arranged to determine the cycle time TD between two successive maximum or two successive minimum values of the instantaneous heart rate data 112. The data processing system 30 may be arranged to set the angular frequency parameter P 202 to value based on cycle time TD directly such that for the determination of the parameters 210, in fitting, the data processing system 30 keeps parameter indicating the angular frequency P 202 of the periodic biofeedback function 200 directly based on the cycle time TD.

Alternatively or additionally, the data processing system 30 may use the value based on the cycle time TD as an initial guess in the search algorithm or fitting method.

Still referring to FIG. 4, in an embodiment, the parameters 210 of the periodic biofeedback function 200 comprise a mean M 205 of the periodic biofeedback function 200. In determining the parameter indicating the mean M 205 of the periodic biofeedback function 200 at the timepoint t, the data processing system 30 is arranged to determine a mean value of the instantaneous heart rate data 112 within the time window w and determine the parameter indicating the mean M 205 of the periodic biofeedback function 200 at the timepoint t based on the mean value. The data processing system 30 may be arranged to set the mean M 205 to the mean value directly such that for the determination of the parameters 210, in fitting, the data processing system 30 keeps the mean M 205 of the periodic biofeedback function 200 based on the mean value.

Alternatively or additionally, the data processing system 30 may use the mean value an initial guess in in the search algorithm.

The amplitude A 201 of the instantaneous heart rate data 112 indicates or determines the heart rate variability of the person 90 in frequency domain (1/time unit) and is thus a frequency domain characterisation. A measure of the heart rate variability in time domain may also be calculated as (1/(M−A))−(1/(M+A))=2A/(M2−A2)≈2A/M2, where A is the amplitude A 201, and M the mean 205.

In an embodiment, and still referring to FIG. 4, the periodic biofeedback function 200 f(t) at a timepoint t comprises a sinusoidal function sin( ) such that f(t) is defined as f(t)=A sin(Pt−T)+M, in which A is the amplitude A 201 of the instantaneous heart rate data 112 within the time window w, P is the angular frequency P 202 of the instantaneous heart rate data 112 within the time window w, T is a time displacement, and M is a mean value M 205 of the instantaneous heart rate data 112 within the time window w. The data processing system 30 may be configured to use the sinusoidal function sin( ) and fit it to the instantaneous heart rate data 112 within the time window w to determine the parameters 210 of the periodic biofeedback function 200 at timepoint t. Through fitting, the parameters A, P and M are determined for the timepoint t within the time window w.

In an embodiment, and referring to FIG. 5, the periodic biofeedback function f(t) 200 at the timepoint t comprises a skewed sinusoidal function sksin( ) such that f(t) is defined as f(t)=A sksin(Pt−T)+M=A sin [(Pt−T)+k*sin(Pt−T)]+M, in which A is the amplitude A 201 of the instantaneous heart rate data 112 within the time window w, P is the angular frequency P 202 of the instantaneous heart rate data 112 within the time window w, T is a time displacement, k is a skew factor, and M is a mean value M 205 of the instantaneous heart rate data 112 within the time window w. The asterisk denotes multiplication. The skew factor k can be set to configure the periodic biofeedback function's 200 waveform to be asymmetric so that rise time (from zero value to the positive or negative amplitude value or peak value) is shorter in time than the fall time from the amplitude value back to the zero value. The skew factor may be 0-1, more advantageously 0.3-0.6 or most advantageously 0.4-0.5. A skewed sinusoidal function is advantageous as the inhalation is often somewhat shorter than the exhalation and thus the asymmetric waveform may easier be fit to the instantaneous heart rate data 112 than a symmetric waveform, symmetry defined relative to the vertical axis of one cycle of the periodic biofeedback function, when said vertical axis located to the timepoint of maximum or minimum value of the function. Through fitting, the parameters A, P and M are determined for the timepoint t within the time window w.

In an embodiment, the periodic biofeedback function 200 at a timepoint t is an alternating trapezoidal pulse train function with an amplitude A and mean value of M.

In an embodiment, that the data processing system 30 is configured to analyse (as operation C) the heart rate measurement data 110 for each heartbeat measured with the heart rate sensor 10.

In another embodiment, the data processing system 30 is configured to analyse, as operation C, the heart rate measurement data 110 for every second heartbeat measured with the heart rate sensor 10.

In another embodiment, the data processing system 30 is configured to analyse, as operation C, the heart rate measurement data 110 such that the frequency of analysis is based on the cumulative difference E 220 such that increasing cumulative difference E 220 makes the frequency of analysis higher, maximally every heartbeat measured with the heart rate sensor 10. Decreasing cumulative difference E 220 makes the frequency of analysis lower such that minimally the data processing system 30 is configured to analyse, as operation C, the heart rate measurement data 110 for every fifth, every tenth of every fifteenth heartbeat measured with the heart rate sensor 10.

Optimal vagus nerve stimulation is achieved when the behaviour of the instantaneous heart rate data 112 is periodic and alternates over time around a mean with a large amplitude A 201. As the instantaneous heart rate data 112 is arranged to be represented by the periodic biofeedback function 200 in the data processing system 30, the cumulative difference E 220 between the periodic biofeedback function 200 and the instantaneous heart rate data 112 may also determine the impact on the vagus nerve stimulation, as the amplitude A 201 may also be large when the periodic biofeedback function 200 does not follow the instantaneous heart rate data 112 well. Thus, as a measure of the ability of the breathing to stimulate vagus nerve, the data processing system 30 may be configured to determine a resonance score 230. As discussed in relation to FIG. 3, and also referring to FIG. **6*a*, in an embodiment, data processing system 30 of system 1 is arranged to determine the resonance score 230 based on the amplitude A 201 of the periodic biofeedback function 200 within the time window w, and the cumulative difference E 220 within the time window w. This is done such that the resonance score 230 may be compared to the predetermined success threshold ET 231 to arrange the breathing pacer to operate in the variable mode 22 or in the controlled mode 21**.

Figure 6A:
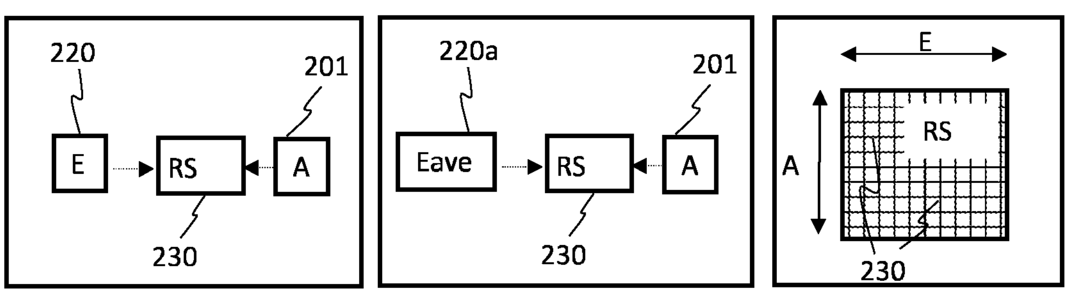

Referring still to FIGS. 3 and 6*a*, in an embodiment, the data processing system 30 of system 1 is arranged to determine the resonance score 230 based on the division of the amplitude A 201 of the periodic biofeedback function 200 within the time window w by an average cumulative difference $E_{AVE}$ 220*a* within the time window w. In other words, the resonance score RS 230 may be defined as a ratio of the amplitude 201 of the periodic biofeedback function, and an average difference $E_{AVE}$ 220*a* of the cumulative difference E 220 of N discrete timepoints within the time window w, $E_{AVE}=E/N$. In other words, $RS=A/E_{AVE}$. In this case, the predetermined success threshold ET 231 may simply be a number to which the resonance score 230 is compared to arrange the breathing pacer to operate in the variable mode 22 or in the controlled mode 21.

The resonance score 230 may also be defined by a two-dimensional table of values for amplitude 201 and cumulative difference E 220. Referring still to FIGS. 3 and 6*a*, in an embodiment, the data processing system 30 of system 1 is arranged to determine the resonance score 230 based on a tabulated and predetermined set of values for resonance score 230, the tabulated and predetermined set of values for resonance score 230 arranged based on the amplitude A 201 of the periodic biofeedback function 200 and cumulative difference E 220 within the time window w. Thus, the resonance score value RS 230 may be pre-recorded or configured for the A and E entries in a table, for example in the data processing system 30, and the data processing system 30 may be arranged to look up the value for the resonance score 230 within the time window w from the table based on the amplitude A 201 of the periodic biofeedback function 200 within the time window w, and cumulative difference E 220 within the time window w. Also in this case, the predetermined success threshold ET 231 may simply be a number to which the resonance score 230 is compared to arrange the breathing pacer to operate in the variable mode 22 or in the controlled mode 21.

Generalizing, any arrangement for the determination of the resonance score 230 that indicates success in the vagus nerve stimulation based on a large value of amplitude A 201 and low value of cumulative difference E 220, and wise versa, is possible, such that the resonance score 230 may be compared to the predetermined success threshold ET 231 to arrange the breathing pacer to operate in the variable mode 22 or in the controlled mode 21.

Figure 6B:
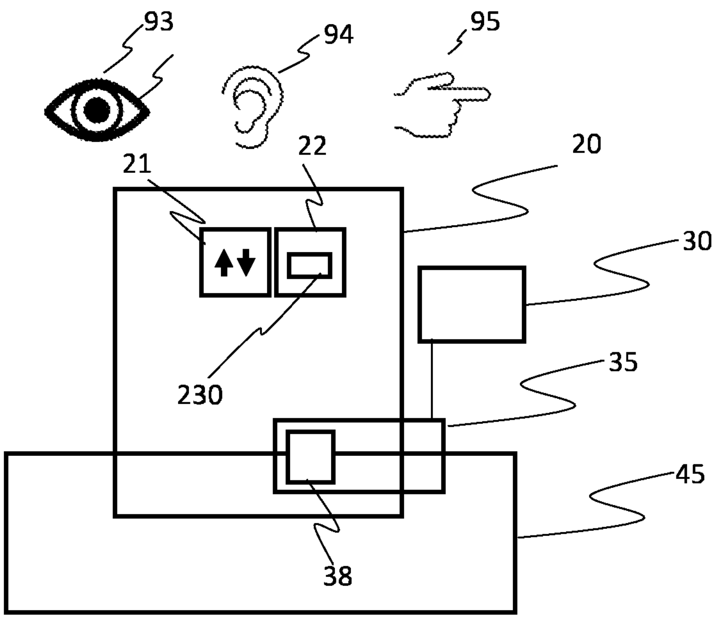

Referring to FIG. 6*b*, in the controlled mode 21, the breathing pacer 20 is configured to time the breathing events to the person 90 visually, as indicated with symbol 93. The breathing pacer 20 may comprise a display, e.g. LCD display, or a lamp or light emitting diode (LED), and visual indication may comprise for example displaying the breathing frequency in which the person is to breathe in the display, or the determination of the moment of controlled breathing with a flashing symbol on the display, or in the lamp or on the LED.

Referring to FIG. 6*b*, in an embodiment, in the controlled mode 21, the breathing pacer 20 is configured to time the breathing events to the person 90 audially, as indicated with a symbol 94. For example, the breathing pacer 20 may comprise a loudspeaker and the breathing pacer 20 may be configured to emit an audio signal for each breath to take in a controlled way, or to play a certain tune based on if the breathing frequency should be increased or decreased by the person.

Referring to FIG. 6*b*, in an embodiment, in the controlled mode 21, the breathing pacer 20 is configured to time the breathing events to the person 90 haptically, as indicated with a symbol 95. For example, the breathing pacer 20 may comprise a linear resonant actuator (LRA), and the breathing pacer 20 may be configured to emit a haptic vibration signal, for example be configured to generate vibrations for each breath the person is to take.

In the controlled mode 21, in an embodiment, the breathing pacer 20 may also be configured to time the breathing events to the person 90 with any combination of audial, haptic or visual feedback, for example by providing a readout of the breathing frequency, flash a symbol when an inhalation is to be taken, emit a beep as an audial signal when a breath is to be taken and also emit a haptic buzz for a breath to take.

Referring to FIG. 6*b*, in an embodiment, in the variable mode 22, the breathing pacer 20 is configured to present information based on the resonance score 230 to the person 90 visually, as also indicated with symbol 93. The breathing pacer 20 may comprise a display, e.g. LCD display, or a lamp or light emitting diode (LED), and presentation may comprise for example displaying the resonance score 230 on the display as numbers or text, or blink the LED or lamp to indicate how optimal the breathing is in relation to the vagus nerve stimulation (e.g. slow blinking indicative of good stimulation, fast blinking indicative of poor vagus nerve stimulation).

Referring still to FIG. 6*b*, in an embodiment, in the variable mode 22, the breathing pacer 20 is configured to present information based on the resonance score 230 to the person 90 audially, as with symbol 94. For example, the breathing pacer 20 may comprise a loudspeaker and the breathing pacer 20 may be configured to emit an audio signal the pitch of which determines how well the vagus nerve stimulus is achieved.

Referring still to FIG. 6*b*, in an embodiment, in the variable mode 22, the breathing pacer 20 is configured to present information based on the resonance score 230 to the person 90 haptically, as with symbol 95. For example, the breathing pacer 20 may comprise a linear resonant actuator (LRA), and the breathing pacer 20 may be configured to emit a haptic “buzzing” signal, such that low frequency of the haptic signal is indicative of a strong vagus nerve stimulation, and high frequency is indicative of a weak vagus nerve stimulation.

Referring still to FIG. 6*b*, in an embodiment, in the variable mode 22 the breathing pacer 20 is configured to present information based on the resonance score 230 with any combination of audial, haptic or visual feedback, for example by providing a readout of the resonance score 230, emit a beep as an audial signal the frequency of which being indicative of the resonance score 230, and also emit a haptic buzz, the frequency of which being indicative of the resonance score 230.

Still referring to FIG. 6*b*, in an embodiment, in the system 1, the breathing pacer 20 comprises third software means 35 executable on a mobile computing device 45. The third software means 35 are functionally connectable with the data processing system 30, and the third software means 35 comprises computer-executable instructions 38 for operating the breathing pacer 20 in the controlled mode 21, the controlled mode 21 comprising timing the breathing events to the person 90. The third software means 35 also comprises computer-executable instructions 38 for operating the breathing pacer 20 in the variable mode 22, the variable mode 22 comprising indicating information related to a resonance score RS 230 to the person 90.

Thus, the functionality of the breathing pacer 20 may be implemented as an application or "app" in a mobile computing device 45, like a smartphone or a tablet computer. Mobile computing devices may comprise a display, a loudspeaker and a haptic feedback device for operation in the controlled mode 21 and in the variable mode 22.

Figure 6C:
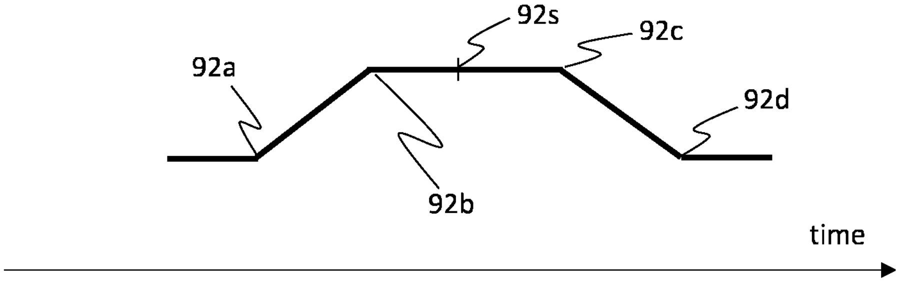

A "breathing cycle" means a respiratory cycle in the present text. One breathing cycle is one sequence of inhalation and exhalation. During the health monitoring session s, the person takes one or more breaths, for example 10, 30, 50 or 70 breaths, one breath corresponding to one breathing cycle. FIG. 6*c* shows schematically the volume of the lungs (vertical y-axis) of the person 90 during one breathing cycle, over time (horizontal x-axis), comprising start of an inhalation 92*a*, end of an inhalation 92*b*, start of an exhalation 92*c* and end of an exhalation 92*d*.

In an embodiment, and referring to FIG. 6*c*, in the system 1, in the controlled mode 21, the breathing pacer 20 is arranged to time the breathing event to the person 90 by indicating to the person 90 a start 92*a* of an inhalation of each breathing cycle.

In an embodiment, and referring to FIG. 6*c*, in the system 1, in the controlled mode 21, the breathing pacer 20 is arranged to time the breathing event to the person 90 by indicating to the person 90 an end 92*b* of an inhalation of each breathing cycle.

In an embodiment, and referring to FIG. 6*c*, in the system 1, in the controlled mode 21, the breathing pacer 20 is arranged to time the breathing event to the person 90 by indicating to the person 90 a start 92*c* of an exhalation of each breathing cycle.

In an embodiment, and referring to FIG. 6*c*, in the system 1, in the controlled mode 21, the breathing pacer 20 is arranged to time the breathing event to the person 90 by indicating to the person 90 an end 92*d* of an exhalation of each breathing cycle.

In an embodiment, and still referring to FIG. 6*c*, in the system 1, in the controlled mode 21, the breathing pacer 20 is arranged to time the breathing event to the person 90 by indicating to the person 90 any combination of the start of an inhalation 92*a*, the end of an inhalation 92*b*, the start of an exhalation 92*c* and the end of an exhalation 92*d*. A good control of breathing is achieved for example by indicating to the person the start of the inhalation 92*a* and the start of the exhalation 92*c*.

In an embodiment, and still referring to FIG. 6*c*, in the system 1, in the controlled mode 21, the breathing pacer 20 is arranged to time the breathing event to the person 90 by indicating to the person 90 a same moment of the breathing cycle 92*s* for every breathing cycle timed by the breathing pacer 20.

Figure 7:
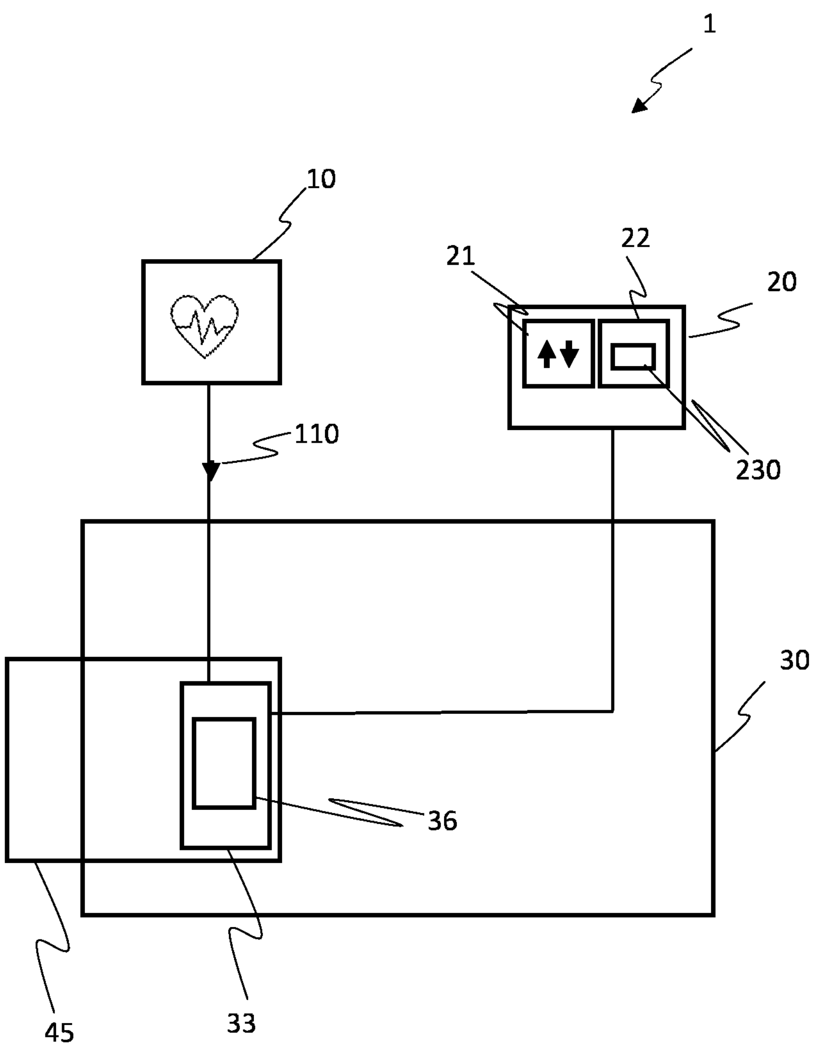
FIG. 7 shows schematically concepts related to another embodiment of the system.

Next referring to FIG. 7, in an embodiment, in the system 1, the data processing system 30 comprises first software means 33 executable on a mobile computing device 45, the first software means 33 being functionally connectable with the heart rate sensor 10, and the first software means 33 comprises computer-executable instructions 36 to receive A the heart rate measurement data, analyse C the heart rate measurement data, and D arrange the breathing pacer 20 into the controlled mode 21, and E arrange the breathing pacer 20 into the variable mode 22. Thus, the data processing system 30 may be arranged to be implemented through software means for example in a smartphone or a tablet computer.

As the breathing pacer 20 and the data processing system 30 may be implemented in the same unit, e.g. a mobile computing device 45, the breathing pacer 20 and the data processing system 30 may be functionally connected through the digital data processing units like memories, information busses, microcontrollers and microprocessors of the mobile computing device 45.

Figure 8:
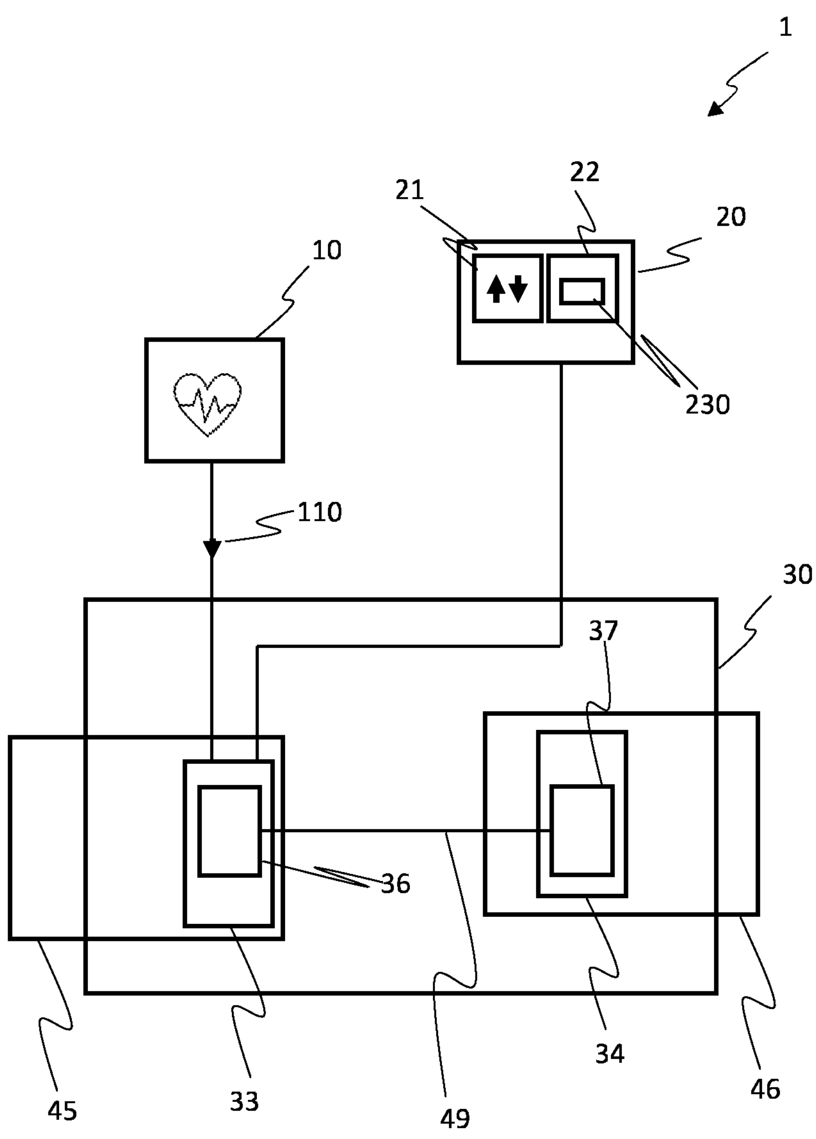
FIG. 8 shows schematically concepts related to yet another embodiment of the system.

Next referring to FIG. 8, in an embodiment, in the system 1, the data processing system 30 comprises second software means 34 executable on a network data server 46, the first software means 33 and the second software means 34 are configured to exchange data over a network connection 49, and the second software means 34 comprises computer-executable instructions 37 to receive A the heart rate measurement data, analyse C the heart rate measurement data, D arrange the breathing pacer 20 into the controlled mode 21, and E arrange the breathing pacer 20 into the variable mode 22. The network connection 49 may comprise physical conductors or a radio interface or both, and it may be arranged through one or more of the standards of ethernet, wireless LAN, Bluetooth, GSM, 3GPP or other cable-based or wireless standard. The network data server 46 may be a server cluster of computers, or an internet cloud network computer center.

In an embodiment, in the system 1, the second software means 34 comprises computer-executable instructions 37 for displaying information based on the parameters 210 of the periodic biofeedback function 200 and the cumulative difference E 220. This is advantageous for example if the health monitoring results are to be published for example over the internet or in an app of a smartphone sharing information over the internet.

Figure 9:
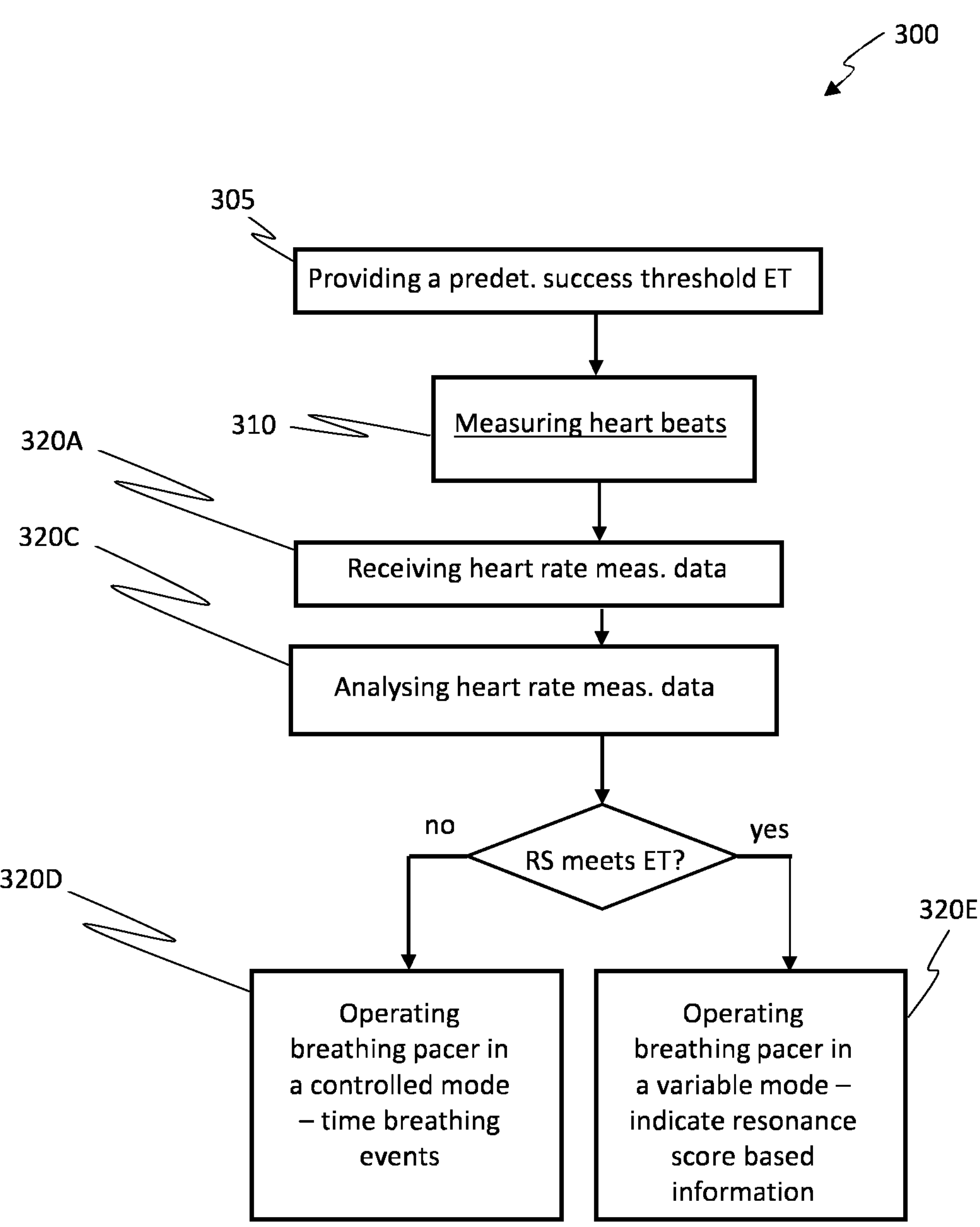
FIG. 9 shows schematically an embodiment of the method according to the current invention.

Next referring to FIG. 9 and also to FIG. 1, as an aspect of the invention, a method 300 for monitoring health of a person 90 during a health monitoring session s is disclosed. The method 300 comprises providing (as step 305) a predetermined success threshold ET 231. The predetermined success threshold 231 is a measure that determines in which mode the breathing pacer 20 operates. The method 300 comprises measuring (as step 310) heart beats of the person 90 for providing heart rate measurement data 110 with a heart rate sensor 10. The method also comprises indicating breathing information to the person 90 with a breathing pacer 20. Breathing information is indicated by operating the breathing pacer 20 in two different modes: in a controlled mode 21 which comprises timing breathing events to the person 90, and in a variable mode 22 that comprises indicating information based on a resonance score RS 230 to the person 90. Timing of the breathing events and indicating information related to a resonance score 230 are already described in the system aspects of the present invention. Information related to a resonance score 230 may be any information of the health effects of the health monitoring session and of the breathing that may be derived from the resonance score 230. Thus, the information related to a resonance score may be the resonance score 230 directly, or it may be another indication of the effectivity of the breathing in vagus nerve stimulation that is based on the resonance score 230, for example text arranged to indicate "strong vagus never stimulation", "good vagus never stimulation" or "weak vagus never stimulation".

The method further comprises receiving (as step 320A) the heart rate measurement data 110 from the heart rate sensor 10 into a data processing system 30, and analysing (as step 320C) the heart rate measurement data 110 in the data processing system 30.

Figure 10A:
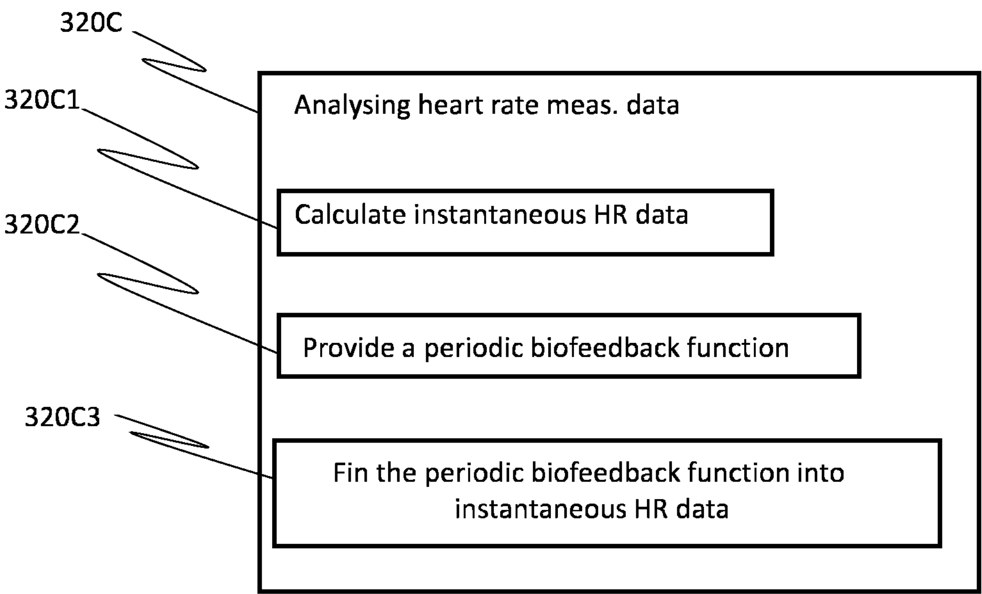
FIGS. 10*a* and 10*b* shows schematically another embodiment of the method according to the current invention.

Referring next to FIG. 10*a*, in step 320C, the following steps (320C1-320C3) are executed in the method 300:

Calculating (as step 320C1) instantaneous heart rate data 112 comprising heart rate of each measured heartbeat. Calculating is performed over a time window w in the health monitoring session s, and the time window w comprises a timepoint t. The instantaneous the heart rate data 112 is calculated based on the heart rate measurement data 110 received from the heart rate sensor 10, providing (as step 320C2) a periodic biofeedback function 200 comprising parameters 210, the parameters 210 comprising an amplitude A 201, the periodic biofeedback function 200 comprising a cumulative difference E 220 relative to the instantaneous heart rate data 112, fitting (as step 320C3) the periodic biofeedback function 200 into the instantaneous heart rate data 112 within the time window w to determine the parameters 210 of the periodic biofeedback function 200 at the timepoint t, the cumulative difference E 220 at the timepoint t, and the resonance score RS 230 at the timepoint t from the parameters 210 and from the cumulative difference E 220, both the parameters 210 and the cumulative difference E 220 at the timepoint t. Thus, step 320C comprises the steps 320C1, 320C2 and 320C3.

Turning back to FIG. 9, the method 300 comprises further operating (as step 320D) the breathing pacer 20 in the controlled mode 21 to time the breathing events to the person 90, if the resonance score RS 230 does not meet the predetermined success threshold ET 231, the resonance score RS 230 meaning here the resonance score RS 230 at the timepoint t. The resonance score RS 230 is determined by receiving A and analysing C the heart rate measurement data 110.

The method 300 comprises further operating (as step 320E) the breathing pacer 20 in the variable mode 22, if the resonance score RS 230 meets the predetermined success threshold ET 231, the resonance score RS 230 meaning here the resonance score RS 230 at the timepoint t. The resonance score RS 230 is determined by receiving A and analysing C the heart rate measurement data 110.

The method may comprise also repeating the steps mentioned above for the duration of the health monitoring session s, for a plurality of time windows w. Thus, the health monitoring session s may comprise a plurality of time windows w, each comprising a timepoint t. In other words, steps 320A, 320C (320C1-320C3), 320D and 320E may be repeated for the duration of the health monitoring session s for a plurality of time windows w.

Figure 10B:
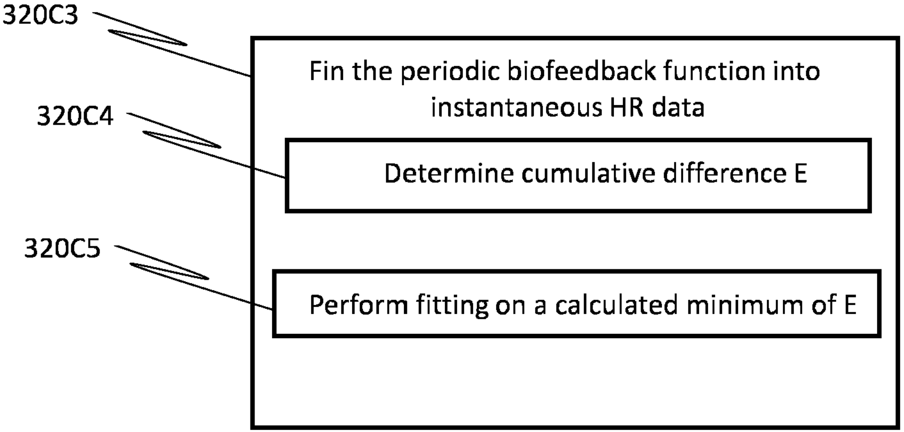

Referring next to FIG. 10*b*, as an embodiment, in the fitting, in step 320C3, the method 300 comprises determining, in step 320C4, a cumulative difference E 220 between the instantaneous heart rate data 112 and the periodic biofeedback function 200 within the time window w comprising the timepoint t, and performing, in step 320C5, the fitting based on a calculated minimum of the cumulative difference E 220 within the time window w to determine the parameters 210 of the periodic biofeedback function 200 at the timepoint t, the time window w comprising the timepoint t.

The method 300 may also comprise, after step 320C5, determining the cumulative difference E 220 at the timepoint t from the calculated minimum of the cumulative difference E 220 within the time window w.

The method 300 may also comprise, after step 320C5, setting the value of the cumulative difference E 220 at the timepoint t to the value of the calculated minimum of the cumulative difference E 220 within the time window w. In other words, after the fitting, the cumulative difference E 220 may have a minimum value within the time window w.

In an embodiment, in step 320C5, the method 300 comprises performing the fitting with a least squares method, a modified least squares method, a random search, an exhaustive search, or any combination thereof. Operation of these methods is discussed above in relation to system 1.

In an embodiment, and referring back to FIG. 4, in the method 300, the periodic biofeedback function f(t) 200 at a timepoint (t) comprises sinusoidal function sin( ) such that f(t) is defined as f(t)=A sin(Pt−T)+M, in which A is the amplitude A 201 of the heart instantaneous heart rate data 112 within the time window w, P is the angular frequency P 202 of the heart instantaneous heart rate data 112 within the time window w, T is a time displacement, and M is a mean value M 205 of the instantaneous heart rate data 112.

In an embodiment, and referring back to FIG. 5, in the method 300, the periodic biofeedback function f(t) 200 at the timepoint (t) comprises a skewed sinusoidal function sksin( ) such that f(t) is defined as f(t)=A sksin(Pt−T)+M=A sin[(Pt−T)+k*sin(Pt−T)], in which A is the amplitude A 201 of the instantaneous heart rate data 112 within the time window w, P is the angular frequency P 202 of the heart instantaneous heart rate data 112 within the time window w, T is a time displacement, k is a skew factor, and M is a mean value M 205 of the instantaneous heart rate data 112 within the time window w. The skew factor k can be set to configure the periodic biofeedback function waveform asymmetric so that, for example, rise time (from zero value to the positive or negative amplitude value or peak value) is shorter in time than the fall time from the amplitude value back to the zero value. This is advantageous as the inhalation is often somewhat shorter than the exhalation and thus the asymmetric waveform may easier be fit to the instantaneous heart rate data 112.

In an embodiment, as illustrated in FIGS. 3 and 6*a*, the method 300 comprises determining the resonance score 230 based on the amplitude A 201 of the periodic biofeedback function 200 within the time window w, and the cumulative difference E 220 within the time window w.

In an embodiment, as illustrated in FIGS. 3 and 6*a*, the method 300 comprises determining the resonance score 230 based on the division of the amplitude A 201 of the periodic biofeedback function 200 within the time window w by an average cumulative difference $E_{AVE}$ 220*a* within the time window w. The average cumulative difference $E_{AVE}$ 220*a* may be calculated by dividing the cumulative difference E 220 by the number of discrete datapoints N used to determine the cumulative difference E 220 as illustrated in relation to FIG. 3.

In an embodiment, as illustrated in FIGS. 3 and 6*a*, the method 300 comprises determining the resonance score 230 based on a tabulated and predetermined set of values for resonance score 230, the tabulated and predetermined set of values for resonance score 230 arranged based on the amplitude A 201 of the periodic biofeedback function 200 within the time window w, and the cumulative difference E 220 within the time window w. Thus, the resonance score value RS 230 may be pre-recorded or configured for the A and E entries in a table, for example in the data processing system 30, and the value for the resonance score 230 may then be looked up from the table based on the amplitude A 201 of the periodic biofeedback function 200 within the time window w, and cumulative difference E 220 within the time window w.

In an embodiment, as illustrated in FIG. 6*b*, when operating the breathing pacer 20 in the controlled mode 21, the controlled mode 21 comprises timing the breathing events to the person 90 visually 93, or audially 94, or haptically 95, or with any combination of visual, audial and haptic indication of timing.

In an embodiment, as illustrated in FIG. 6*b*, when operating the breathing pacer 20 in the variable mode 22 the variable mode 22 comprises indicating information related to a resonance score RS 230 to the person 90 visually 93, or audially 94, or haptically 95, with or any combination of visual, audial and haptic indication of timing.

As an aspect of the invention, the method 300 defined above may be executed in the system 1 as defined above.

Figure 11:
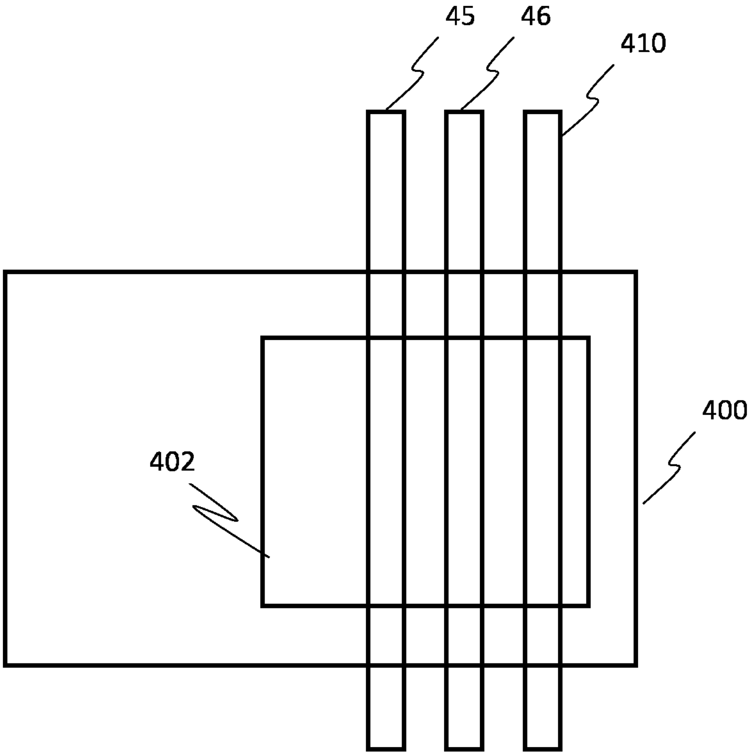
FIG. 11 shows schematically aspects of a computer program according to an aspect of the current invention.

Next turning to FIG. 11, as an aspect of the present invention, a computer program 400 comprises executable instructions 402 which are configured to execute the steps of the method 300 in a computer 410, or in a mobile computing device 45 or network data server 46, or any combination thereof.

For the purposes of this text, the data processing system 30 may comprise digital electronics, analogue electronics, memory or memories, power unit like a battery, ASICs, FPGAs, digital busses, microcontrollers and microprocessors to arrange its various operations. The data processing system 30 may also comprise one or more input devices like a keyboard, a microphone or a touch screen display, and output devices like a LED, a display, a loudspeaker or a haptic device like a linear resonant actuator. The data processing system 30 may be arranged in a mobile computing device like a smartphone or tablet computer, for example through software and hardware means. If the heart rate measurement data from the heart rate sensor 10 is in analogue format, the data processing system 30 may also comprise analogue-to-digital converters to arrange conversion of an analogue signal into a digital signal for further processing.

The invention has been described above with reference to the examples shown in the figures. However, the invention is in no way restricted to the above examples but may vary within the scope of the claims.

The invention claimed is:

1. A system for monitoring health of a person during a health monitoring session(s), wherein the system comprises:

a heart rate sensor configured to measure heart beats of the person for providing heart rate measurement data, a breathing pacer configured to indicate breathing information to the person, the breathing pacer configured to operate in:

a controlled mode comprising timing breathing events to the person, in the controlled mode the breathing pacer is configured to operate at a predetermined breathing frequency and to indicate the breathing events to the person, and a variable mode comprising indicating information related to a resonance score (RS) to the person, in the variable mode the system is configured to determine the breathing frequency of the person based on the received heart rate measurement data and in the variable mode the breathing pacer is configured to indicate the determined breathing frequency to the person;

a data processing system arranged configured to provide a predetermined success threshold (ET), the data processing system configured, during the health monitoring session(s), to receive (A) the heart rate measurement data from the heart rate sensor, analyze (C) the heart rate measurement data such that in the analysis, the data processing system is configured to:

calculate (C1) instantaneous heart rate data comprising heart rate of each measured heartbeat, calculating is performed over a time window (w) in the health monitoring session(s), the time window (w) comprising a timepoint (t), the instantaneous heart rate data being calculated based on the heart rate measurement data received from the heart rate sensor, provide (C2) a periodic biofeedback function comprising parameters, the parameters of the periodic biofeedback function comprising an amplitude (A), fit (C3) the periodic biofeedback function into the instantaneous heart rate data within the time window (w) to determine the parameters of the periodic biofeedback function at the timepoint (t), a cumulative difference (E) between the instantaneous heart rate data and the periodic biofeedback function within the time window (w) at the timepoint (t), and the resonance score (RS) at the timepoint (t) from the parameters and from the cumulative difference (E);

operate the breathing pacer in the controlled mode to time the breathing events to the person if the resonance score (RS) does not meet the predetermined success threshold (ET), the resonance score (RS) determined by receiving (A) and analyzing (C) the heart rate measurement data, and operate the breathing pacer in the variable mode if the resonance score (RS) meets the predetermined success threshold (ET), the resonance score (RS) determined by receiving (A) and analyzing (C) the heart rate measurement data.

2. The system according to claim 1, wherein the data processing system is configured to:

determine the cumulative difference (E) between the instantaneous heart rate data and the periodic biofeedback function within the time window (w), and perform the fitting (C3) based on a calculated minimum of the cumulative difference (E) within the time window (w) to determine the parameters of the periodic biofeedback function at the timepoint (t).

3. The system according to claim 2, wherein the data processing system is configured to perform the fitting (C3) within the time window (w) with:

a least squares method; or a modified least squares method; or a random search; or an exhaustive search; or any combination thereof.

4. The system according to claim 1, wherein (C3), in determining the parameter indicating the amplitude (A) of the periodic biofeedback function at the timepoint (t), the data processing system is configured to:

determine a minimum instantaneous heart rate and a maximum instantaneous heart rate of the instantaneous heart rate data within the time window (w), subtract the minimum instantaneous heart rate from the maximum instantaneous heart rate, divide a value of the subtraction by 2, and determine the parameter indicating the amplitude (A) of the periodic biofeedback function at the timepoint (t) based on a value of the division.

5. The system according to claim 1, wherein the parameters of the periodic biofeedback function comprise an angular frequency (P), and in fitting (C3), in determining the parameter indicating the angular frequency (P) of the periodic biofeedback function at the timepoint (t), the data processing system is configured to:

determine a cycle time (TD) of the instantaneous heart rate data within the time window (w), and determine the parameter indicating the angular frequency (P) of the periodic biofeedback function at the timepoint (t) based on the cycle time (TD).

6. The system according to claim 1, wherein:

the parameters of the periodic biofeedback function comprise a mean (M) of the periodic biofeedback function, and in fitting (C3), in determining the mean (M) of the periodic biofeedback function at the timepoint (t), the data processing system is configured to:

determine a mean value of the instantaneous heart rate data within the time window (w), and determine the mean (M) of the periodic biofeedback function at the timepoint (t) based on the mean value.

7. The system according to claim 1, wherein:

the periodic biofeedback function f(t) at the timepoint (t) comprises a sinusoidal function sin( ) such that f(t) is defined as $f(t)=A \sin(Pt-T)+M$, wherein:

A is the amplitude (A) of the instantaneous heart rate data within the time window (w), P is an angular frequency (P) of the instantaneous heart rate data within the time window (w), T is a time displacement, and M is a mean value (M) of the instantaneous heart rate data within the time window (w); or the periodic biofeedback function f(t) at the timepoint (t) comprises a skewed sinusoidal function sksin( ) such that f(t) is defined as $f(t)=A\,\mathrm{sksin}(Pt-T)+M=A \sin[(Pt-T)+k*\sin(Pt-T)]+M$, wherein A is the amplitude (A) of the instantaneous heart rate data within the time window (w), P is an angular frequency (P) of the instantaneous heart rate data within the time window (w), T is a time displacement, k is a skew factor, and M is a mean value (M) of the instantaneous heart rate data within the time window (w).

8. The system according to claim 1, wherein the data processing system is configured to analyze (C) the heart rate measurement data for each heartbeat measured with the heart rate sensor.

9. The system according to claim 1, wherein the data processing system is configured to determine the resonance score (RS):

based on the amplitude (A) of the periodic biofeedback function and the cumulative difference (E) within the time window (w); or based on a division of the amplitude (A) of the periodic biofeedback function by an average cumulative difference (EAVE) within the time window (w); or based on a predetermined set of values that associates resonance score values with the amplitude (A) of the periodic biofeedback function and the cumulative difference (E) within the time window (w).

10. The system according to claim 1, wherein in the controlled mode, the breathing pacer is configured to time the breathing events to the person by at least one of:

visually; or audially; or haptically; or any combination thereof.

11. The system according to claim 1, wherein in the variable mode, the breathing pacer is configured to present information based on the resonance score (RS) to the person by at least one of:

visually; or audially; or haptically; or any combination thereof.

12. The system according to claim 9, wherein:

the breathing pacer comprises third software means executable on a mobile computing device, and the third software means are functionally connectable with the data processing system, and the third software means comprises computer-executable instructions for operating the breathing pacer in the controlled mode, the controlled mode comprising timing the breathing events to the person, and in the variable mode, the variable mode comprising indicating information related to the resonance score (RS) to the person.

13. The system according to claim 1, wherein in the controlled mode, the breathing pacer is configured to time the breathing events to the person by indicating to the person by at least one of:

a start of an inhalation of each breathing cycle; or an end of an inhalation of each breathing cycle; or a start of an exhalation of each breathing cycle; or an end of an exhalation of each breathing cycle; or any combination thereof.

14. The system according to claim 1, wherein:

the data processing system comprises first software means executable on a mobile computing device, the first software means being functionally connectable with the heart rate sensor, and the first software means comprises computer-executable instructions to receive the heart rate measurement data, analyze the heart rate measurement data, arrange the breathing pacer in the controlled mode, and arrange the breathing pacer in the variable mode.

15. The system according to claim 14, wherein:

the data processing system comprises second software means executable on a network data server, the first software means and the second software means are configured to exchange data over a network connection, and the second software means comprises computer-executable instructions to receive the heart rate measurement data, analyze (C) the heart rate measurement data, arrange the breathing pacer in the controlled mode, and arrange the breathing pacer in the variable mode.

16. The system according to claim 15, wherein:

the second software means comprises computer-executable instructions for displaying information based on the parameters of the periodic biofeedback function and the cumulative difference (E).

17. A method for monitoring health of a person during a health monitoring session(s), wherein the method comprises:

providing a predetermined success threshold (ET), measuring heart beats of the person for providing heart rate measurement data with a heart rate sensor, indicating breathing information to the person with a breathing pacer by operating the breathing pacer in a controlled mode, the controlled mode comprising timing breathing events to the person, and in the controlled mode, operating the breathing pacer at a predetermined breathing frequency and indicating the breathing events to the person, and in a variable mode, the variable mode comprising indicating information related to a resonance score (RS) to the person, determining the breathing frequency of the person based on the received heart rate measurement data, and indicating the determined breathing frequency to the person, receiving (A) the heart rate measurement data from the heart rate sensor into a data processing system, analyzing (C) the heart rate measurement data in the data processing system by calculating (C1) instantaneous heart rate data comprising heart rate of each measured heartbeat, calculating is performed over a time window (w) in the health monitoring session(s), the time window (w) comprising a timepoint (t), the instantaneous heart rate data being calculated based on the heart rate measurement data received from the heart rate sensor, providing (C2) a periodic biofeedback function comprising parameters, the parameters comprising an amplitude (A), fitting (C3) the periodic biofeedback function into the instantaneous heart rate data within the time window (w) to determine the parameters of the periodic biofeedback function at the timepoint (t), a cumulative difference (E) between the instantaneous heart rate data and the periodic biofeedback function within the time window (w) at the timepoint (t), and the resonance score (RS) at the timepoint (t) from the parameters and from the cumulative difference (E), operating the breathing pacer in the controlled mode to time the breathing events to the person if the resonance score (RS) does not meet the predetermined success threshold (ET), the resonance score (RS) determined by receiving (A) and analyzing (C) the heart rate measurement data, and operating the breathing pacer in the variable mode if the resonance score (RS) meets the predetermined success threshold (ET), the resonance score (RS) determined by receiving (A) and analyzing (C) the heart rate measurement data.

18. A processor-readable medium storing instructions which, when executed by at least one processor of an apparatus, cause the apparatus at least to perform the method according to claim 17.

* * * * *